United States Patent
Kostrzewski et al.

(10) Patent No.: US 10,709,901 B2
(45) Date of Patent: Jul. 14, 2020

(54) IMPLANTABLE FASTENERS, APPLICATORS, AND METHODS FOR BRACHYTHERAPY

(71) Applicant: Covidien LP, Mansfield, MA (US)

(72) Inventors: Stanislaw Kostrzewski, Newton, CT (US); Gerald Hodgkinson, Guilford, CT (US); Lee Ann Olson, Wallingford, CT (US); Russell Pribanic, Roxbury, CT (US); Matthew Chowaniec, Madison, CT (US); Robert Pedros, Oxford, CT (US); Thomas Campanelli, Oxford, CT (US); David Nicholas, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 242 days.

(21) Appl. No.: 15/835,853

(22) Filed: Dec. 8, 2017

(65) Prior Publication Data

US 2018/0185670 A1    Jul. 5, 2018

Related U.S. Application Data

(60) Provisional application No. 62/514,089, filed on Jun. 2, 2017, provisional application No. 62/451,936, filed
(Continued)

(51) Int. Cl.
*A61N 5/10* (2006.01)
*A61B 17/068* (2006.01)
(Continued)

(52) U.S. Cl.
CPC .......... *A61N 5/1027* (2013.01); *A61B 17/068* (2013.01); *A61B 17/0644* (2013.01);
(Continued)

(58) Field of Classification Search
CPC ............ A61N 5/1001; A61N 2005/101; A61N 5/1015; A61N 5/1007; A61N 2005/1024;
(Continued)

(56) References Cited

U.S. PATENT DOCUMENTS 3,079,606 A    3/1963    Bobrov et al.
3,490,675 A    1/1970    Green et al.
(Continued)

FOREIGN PATENT DOCUMENTS

AU    198654765    9/1986
CA    2773414 A1    11/2012
(Continued)

OTHER PUBLICATIONS

Extended European Search Report issued in corresponding European Application No. 18150357.4 dated Mar. 29, 2018.
(Continued)

*Primary Examiner* — Navin Natnithithadha
*Assistant Examiner* — Sunita Reddy
(74) *Attorney, Agent, or Firm* — Carter, DeLuca & Farrell LLP

(57) ABSTRACT

A fastener applicator includes a body portion including a handle assembly, a cartridge assembly supported within the body portion, the cartridge assembly including implantable fasteners, a drive assembly supported within the body portion and operatively coupled to the cartridge assembly to engage the implantable fasteners, and an actuation assembly supported within the handle assembly and operatively coupled to the drive assembly to fire a distal-most implantable fastener upon actuation of the actuation assembly. At least one of the implantable fasteners includes a body including a tissue facing surface, a tissue penetrating portion
(Continued)

extending from the body, and a capsule affixed to the tissue facing surface of the body, the capsule including radioactive material.

10 Claims, 13 Drawing Sheets

Related U.S. Application Data on Jan. 30, 2017, provisional application No. 62/442,610, filed on Jan. 5, 2017.

(51) Int. Cl.
   *A61B 17/064* (2006.01)
   *A61M 39/02* (2006.01)
   *A61B 90/00* (2016.01)
   *A61B 17/00* (2006.01)

(52) U.S. Cl.
   CPC ........ *A61B 17/0684* (2013.01); *A61N 5/1001* (2013.01); *A61N 5/1007* (2013.01); *A61B 2017/00004* (2013.01); *A61B 2017/0649* (2013.01); *A61B 2090/3966* (2016.02); *A61M 39/0208* (2013.01); *A61N 5/1015* (2013.01); *A61N 2005/101* (2013.01); *A61N 2005/1024* (2013.01)

(58) Field of Classification Search
   CPC .............. A61N 5/1027; A61B 17/0644; A61B 17/0684; A61B 2017/00004; A61B 2090/3966; A61B 2017/0649; A61B 17/068; A61M 39/0208
   USPC ........................................................ 600/1–8
   See application file for complete search history.

(56) References Cited

U.S. PATENT DOCUMENTS

| | | |
|---|---|---|
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,241,861 A | 12/1980 | Fleischer |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |

(56) References Cited

U.S. PATENT DOCUMENTS

| | | |
|---|---|---|
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huiterna et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,830,221 A | 11/1998 | Stein et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |

(56) References Cited

U.S. PATENT DOCUMENTS

| | | |
|---|---|---|
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,293,899 B1 * | 9/2001 | Sioshansi ............ A61N 5/1001 600/3 |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Willman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |

(56) References Cited

U.S. PATENT DOCUMENTS

| | | |
|---|---|---|
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,630 B2 | 11/2010 | Damadian et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scirica |
| 7,845,537 B2 | 12/2010 | Shelton, IV et al. |

(56) References Cited

U.S. PATENT DOCUMENTS

| | | |
|---|---|---|
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |

(56) References Cited

U.S. PATENT DOCUMENTS

| | | | |
|---|---|---|---|
| 8,215,532 B2 | 7/2012 | Marczyk | |
| 8,216,236 B2 | 7/2012 | Heinrich et al. | |
| 8,220,688 B2 | 7/2012 | Laurent et al. | |
| 8,220,690 B2 | 7/2012 | Hess et al. | |
| 8,225,979 B2 | 7/2012 | Farascioni et al. | |
| 8,231,040 B2 | 7/2012 | Zemlok et al. | |
| 8,231,041 B2 | 7/2012 | Marczyk et al. | |
| 8,235,272 B2 | 8/2012 | Nicholas et al. | |
| 8,235,273 B2 | 8/2012 | Olson et al. | |
| 8,235,274 B2 | 8/2012 | Cappola | |
| 8,236,010 B2 | 8/2012 | Ortiz et al. | |
| 8,240,536 B2 | 8/2012 | Marczyk | |
| 8,240,537 B2 | 8/2012 | Marczyk | |
| 8,241,322 B2 | 8/2012 | Whitman et al. | |
| 8,245,897 B2 | 8/2012 | Tzakis et al. | |
| 8,245,898 B2 | 8/2012 | Smith et al. | |
| 8,245,899 B2 | 8/2012 | Swensgard et al. | |
| 8,245,931 B2 | 8/2012 | Shigeta | |
| 8,252,009 B2 | 8/2012 | Weller et al. | |
| 8,256,653 B2 | 9/2012 | Farascioni | |
| 8,256,654 B2 | 9/2012 | Bettuchi et al. | |
| 8,256,655 B2 | 9/2012 | Sniffin et al. | |
| 8,256,656 B2 | 9/2012 | Milliman et al. | |
| 8,267,300 B2 | 9/2012 | Boudreaux | |
| 8,272,551 B2 | 9/2012 | Knodel et al. | |
| 8,272,553 B2 | 9/2012 | Mastri et al. | |
| 8,272,554 B2 | 9/2012 | Whitman et al. | |
| 8,276,594 B2 | 10/2012 | Shah | |
| 8,276,801 B2 | 10/2012 | Zemlok et al. | |
| 8,281,973 B2 | 10/2012 | Wenchell et al. | |
| 8,286,847 B2 | 10/2012 | Taylor | |
| 8,286,848 B2 | 10/2012 | Wenchell et al. | |
| 8,286,850 B2 | 10/2012 | Viola | |
| 8,292,146 B2 | 10/2012 | Holsten et al. | |
| 8,292,147 B2 | 10/2012 | Viola | |
| 8,292,148 B2 | 10/2012 | Viola | |
| 8,292,149 B2 | 10/2012 | Ivanko | |
| 8,292,150 B2 | 10/2012 | Bryant | |
| 8,292,151 B2 | 10/2012 | Viola | |
| 8,292,152 B2 | 10/2012 | Milliman et al. | |
| 8,292,153 B2 | 10/2012 | Jankowski | |
| 8,292,154 B2 | 10/2012 | Marczyk | |
| 8,292,155 B2 | 10/2012 | Shelton, IV et al. | |
| 8,292,156 B2 | 10/2012 | Kostrzewski | |
| 8,292,158 B2 | 10/2012 | Sapienza | |
| 8,308,040 B2 | 11/2012 | Huang et al. | |
| 8,308,041 B2 | 11/2012 | Kostrzewski | |
| 8,308,042 B2 | 11/2012 | Aranyi | |
| 8,308,043 B2 | 11/2012 | Bindra et al. | |
| 8,308,044 B2 | 11/2012 | Viola | |
| 8,308,046 B2 | 11/2012 | Prommersberger | |
| 8,308,757 B2 | 11/2012 | Hillstead et al. | |
| 8,317,070 B2 | 11/2012 | Hueil et al. | |
| 8,317,071 B1 | 11/2012 | Knodel | |
| 8,322,455 B2 | 12/2012 | Shelton, IV et al. | |
| 8,322,589 B2 | 12/2012 | Boudreaux | |
| 8,328,061 B2 | 12/2012 | Kasvikis | |
| 8,328,065 B2 | 12/2012 | Shah | |
| 8,333,313 B2 | 12/2012 | Boudreaux et al. | |
| 8,336,751 B2 | 12/2012 | Scirica | |
| 8,336,753 B2 | 12/2012 | Olson et al. | |
| 8,336,754 B2 | 12/2012 | Cappola et al. | |
| 8,342,376 B2 * | 1/2013 | Surti | A61B 17/064 227/175.1 |
| 8,342,377 B2 | 1/2013 | Milliman et al. | |
| 8,342,378 B2 | 1/2013 | Marczyk et al. | |
| 8,342,379 B2 | 1/2013 | Whitman et al. | |
| 8,342,380 B2 | 1/2013 | Viola | |
| 8,348,123 B2 | 1/2013 | Scirica et al. | |
| 8,348,124 B2 | 1/2013 | Scirica | |
| 8,348,125 B2 | 1/2013 | Viola et al. | |
| 8,348,126 B2 | 1/2013 | Olson et al. | |
| 8,348,127 B2 | 1/2013 | Marczyk | |
| 8,348,129 B2 | 1/2013 | Bedi et al. | |
| 8,348,130 B2 | 1/2013 | Shah et al. | |
| 8,348,131 B2 | 1/2013 | Omaits et al. | |
| 8,353,437 B2 | 1/2013 | Boudreaux | |
| 8,353,440 B2 | 1/2013 | Whitman et al. | |
| 8,356,740 B1 | 1/2013 | Knodel | |
| 8,357,174 B2 | 1/2013 | Roth et al. | |
| 8,360,294 B2 | 1/2013 | Scirica | |
| 8,360,297 B2 | 1/2013 | Shelton, IV et al. | |
| 8,360,298 B2 | 1/2013 | Farascioni et al. | |
| 8,360,299 B2 | 1/2013 | Zemlok et al. | |
| 8,365,971 B1 | 2/2013 | Knodel | |
| 8,365,972 B2 | 2/2013 | Aranyi et al. | |
| 8,365,973 B1 | 2/2013 | White et al. | |
| 8,365,976 B2 | 2/2013 | Hess et al. | |
| 8,371,491 B2 | 2/2013 | Huitema et al. | |
| 8,371,492 B2 | 2/2013 | Aranyi et al. | |
| 8,371,493 B2 | 2/2013 | Aranyi et al. | |
| 8,381,828 B2 | 2/2013 | Whitman et al. | |
| 8,381,961 B2 | 2/2013 | Holsten et al. | |
| 8,387,848 B2 | 3/2013 | Johnson et al. | |
| 8,387,849 B2 | 3/2013 | Buesseler et al. | |
| 8,387,850 B2 | 3/2013 | Hathaway et al. | |
| 8,388,652 B2 | 3/2013 | Viola | |
| 8,393,513 B2 | 3/2013 | Jankowski | |
| 8,393,514 B2 | 3/2013 | Shelton, IV et al. | |
| 8,393,516 B2 | 3/2013 | Kostrzewski | |
| 8,397,971 B2 | 3/2013 | Yates et al. | |
| 8,397,972 B2 | 3/2013 | Kostrzewski | |
| 8,403,195 B2 | 3/2013 | Beardsley et al. | |
| 8,403,196 B2 | 3/2013 | Beardsley et al. | |
| 8,403,197 B2 | 3/2013 | Vidal et al. | |
| 8,403,198 B2 | 3/2013 | Sorrentino et al. | |
| 8,403,946 B2 | 3/2013 | Whitfield et al. | |
| 8,403,956 B1 | 3/2013 | Thompson et al. | |
| 8,408,439 B2 | 4/2013 | Huang et al. | |
| 8,408,440 B2 | 4/2013 | Olson et al. | |
| 8,408,442 B2 | 4/2013 | Racenet et al. | |
| 8,413,868 B2 | 4/2013 | Cappola | |
| 8,413,869 B2 | 4/2013 | Heinrich | |
| 8,413,871 B2 | 4/2013 | Racenet et al. | |
| 8,418,904 B2 | 4/2013 | Wenchell et al. | |
| 8,418,905 B2 | 4/2013 | Milliman | |
| 8,418,906 B2 | 4/2013 | Farascioni et al. | |
| 8,418,907 B2 | 4/2013 | Johnson et al. | |
| 8,418,908 B1 | 4/2013 | Beardsley | |
| 8,419,768 B2 | 4/2013 | Marczyk | |
| 8,424,735 B2 | 4/2013 | Viola et al. | |
| 8,424,736 B2 | 4/2013 | Scirica et al. | |
| 8,424,737 B2 | 4/2013 | Scirica | |
| 8,424,739 B2 | 4/2013 | Racenet et al. | |
| 8,424,740 B2 | 4/2013 | Shelton, IV et al. | |
| 8,439,244 B2 | 5/2013 | Holcomb et al. | |
| 8,439,245 B2 | 5/2013 | Knodel et al. | |
| 8,439,246 B1 | 5/2013 | Knodel | |
| 8,444,036 B2 | 5/2013 | Shelton, IV | |
| 8,444,037 B2 | 5/2013 | Nicholas et al. | |
| 8,444,038 B2 | 5/2013 | Farascioni et al. | |
| 8,448,832 B2 | 5/2013 | Viola et al. | |
| 8,453,652 B2 | 6/2013 | Stopek | |
| 8,453,905 B2 | 6/2013 | Holcomb et al. | |
| 8,453,906 B2 | 6/2013 | Huang et al. | |
| 8,453,907 B2 | 6/2013 | Laurent et al. | |
| 8,453,908 B2 | 6/2013 | Bedi et al. | |
| 8,453,909 B2 | 6/2013 | Olson et al. | |
| 8,453,910 B2 | 6/2013 | Bettuchi et al. | |
| 8,453,912 B2 | 6/2013 | Mastri et al. | |
| 8,453,913 B2 | 6/2013 | Milliman | |
| 8,453,914 B2 | 6/2013 | Laurent et al. | |
| 8,454,628 B2 | 6/2013 | Smith et al. | |
| 8,459,520 B2 | 6/2013 | Giordano et al. | |
| 8,459,521 B2 | 6/2013 | Zemlok et al. | |
| 8,459,522 B2 | 6/2013 | Marczyk | |
| 8,459,523 B2 | 6/2013 | Whitman | |
| 8,459,524 B2 | 6/2013 | Pribanic et al. | |
| 8,459,525 B2 | 6/2013 | Yates et al. | |
| 8,464,922 B2 | 6/2013 | Marczyk | |
| 8,464,923 B2 | 6/2013 | Shelton, IV | |
| 8,469,252 B2 | 6/2013 | Holcomb et al. | |
| 8,469,254 B2 | 6/2013 | Czernik et al. | |
| 8,474,677 B2 | 7/2013 | Woodard, Jr. et al. | |

(56) References Cited

U.S. PATENT DOCUMENTS

| | | |
|---|---|---|
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | (Prommersberger) Stopek et al. |
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,684,253 B2 | 4/2014 | Giordano et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,752,748 B2 | 6/2014 | Whitman et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,876 B2 | 7/2014 | Kostrzewski |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,631 B2 | 9/2014 | Munro, III et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,788 B2 | 9/2014 | Knodel |
| 8,851,354 B2 | 10/2014 | Swensgard et al. |
| 8,851,355 B2 | 10/2014 | Aranyi et al. |
| 8,857,693 B2 | 10/2014 | Schuckmann et al. |
| 8,864,007 B2 | 10/2014 | Widenhouse et al. |
| 8,864,009 B2 | 10/2014 | Shelton, IV et al. |
| 8,875,971 B2 | 11/2014 | Hall et al. |
| 8,875,972 B2 | 11/2014 | Weisenburgh, II et al. |
| 8,893,949 B2 | 11/2014 | Shelton, IV et al. |
| 8,893,950 B2 | 11/2014 | Marczyk |
| 8,899,461 B2 | 12/2014 | Farascioni |
| 8,899,463 B2 | 12/2014 | Schall et al. |
| 8,899,464 B2 | 12/2014 | Hueil et al. |
| 8,900,616 B2 | 12/2014 | Belcheva et al. |
| 8,920,435 B2 | 12/2014 | Smith et al. |
| 8,925,782 B2 | 1/2015 | Shelton, IV |
| 8,926,598 B2 | 1/2015 | Mollere et al. |
| 8,931,682 B2 | 1/2015 | Timm et al. |
| 8,931,693 B1 | 1/2015 | Kumar et al. |
| 8,939,153 B1 * | 1/2015 | Reicher ............... A61B 5/0031 128/897 |
| 8,955,732 B2 | 2/2015 | Zemlok et al. |
| 8,958,429 B2 | 2/2015 | Shukla et al. |
| 8,960,517 B2 | 2/2015 | Lee |
| 8,967,443 B2 | 3/2015 | McCuen |
| 8,973,803 B2 | 3/2015 | Hall et al. |
| 8,978,954 B2 | 3/2015 | Shelton, IV et al. |

(56) References Cited

U.S. PATENT DOCUMENTS

| | | |
|---|---|---|
| 8,978,956 B2 | 3/2015 | Schall et al. |
| 8,998,060 B2 | 4/2015 | Bruewer et al. |
| 9,005,230 B2 | 4/2015 | Yates et al. |
| 9,010,607 B2 | 4/2015 | Kostrzewski |
| 9,016,539 B2 | 4/2015 | Kostrzewski et al. |
| 9,016,541 B2 | 4/2015 | Viola et al. |
| 9,016,542 B2 | 4/2015 | Shelton, IV et al. |
| 9,016,546 B2 | 4/2015 | Demmy et al. |
| 9,022,271 B2 | 5/2015 | Scirica |
| 9,027,817 B2 | 5/2015 | Milliman et al. |
| 9,033,203 B2 | 5/2015 | Woodard, Jr. et al. |
| 9,044,228 B2 | 6/2015 | Woodard, Jr. et al. |
| 9,044,229 B2 | 6/2015 | Scheib et al. |
| 9,050,084 B2 | 6/2015 | Schmid et al. |
| 9,055,941 B2 | 6/2015 | Schmid et al. |
| 9,060,770 B2 | 6/2015 | Shelton, IV et al. |
| 9,072,535 B2 | 7/2015 | Shelton, IV et al. |
| 9,089,326 B2 | 7/2015 | Krumanaker et al. |
| 9,101,359 B2 | 8/2015 | Smith et al. |
| 9,107,663 B2 | 8/2015 | Swensgard |
| 9,107,664 B2 | 8/2015 | Marczyk |
| 9,113,862 B2 | 8/2015 | Morgan et al. |
| 9,113,864 B2 | 8/2015 | Morgan et al. |
| 9,113,870 B2 | 8/2015 | Viola |
| 9,113,872 B2 | 8/2015 | Viola |
| 9,113,880 B2 | 8/2015 | Zemlok et al. |
| 9,125,649 B2 | 9/2015 | Bruewer et al. |
| 9,138,225 B2 | 9/2015 | Huang et al. |
| 9,155,537 B2 | 10/2015 | Katre et al. |
| 9,179,912 B2 | 11/2015 | Yates et al. |
| 9,192,378 B2 | 11/2015 | Aranyi et al. |
| 9,192,379 B2 | 11/2015 | Aranyi et al. |
| 9,192,384 B2 | 11/2015 | Bettuchi |
| 9,198,644 B2 | 12/2015 | Balek et al. |
| 9,198,654 B1 * | 12/2015 | Reicher ................. A61B 5/0031 |
| 9,198,661 B2 | 12/2015 | Swensgard |
| 9,204,876 B2 | 12/2015 | Cappola et al. |
| 9,216,019 B2 | 12/2015 | Schmid et al. |
| 9,216,020 B2 | 12/2015 | Zhang et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,232,941 B2 | 1/2016 | Mandakolathur Vasudevan et al. |
| 9,232,944 B2 | 1/2016 | Cappola et al. |
| 9,237,891 B2 | 1/2016 | Shelton, IV |
| 9,254,180 B2 | 2/2016 | Huitema et al. |
| 9,265,585 B2 | 2/2016 | Wingardner et al. |
| 9,271,728 B2 | 3/2016 | Gupta et al. |
| 9,277,919 B2 | 3/2016 | Timmer et al. |
| 9,282,962 B2 | 3/2016 | Schmid et al. |
| 9,283,054 B2 | 3/2016 | Morgan et al. |
| 9,289,209 B2 | 3/2016 | Gurumurthy et al. |
| 9,289,210 B2 | 3/2016 | Baxter, III et al. |
| 9,289,225 B2 | 3/2016 | Shelton, IV et al. |
| 9,295,464 B2 | 3/2016 | Shelton, IV et al. |
| 9,295,465 B2 | 3/2016 | Farascioni |
| 9,301,752 B2 | 4/2016 | Mandakolathur Vasudevan et al. |
| 9,301,753 B2 | 4/2016 | Aldridge et al. |
| 9,301,757 B2 | 4/2016 | Williams |
| 9,307,965 B2 | 4/2016 | Ming |
| 9,307,986 B2 | 4/2016 | Hall et al. |
| 9,307,989 B2 | 4/2016 | Shelton, IV et al. |
| 9,314,246 B2 | 4/2016 | Shelton, IV et al. |
| 9,320,518 B2 | 4/2016 | Henderson et al. |
| 9,320,521 B2 | 4/2016 | Shelton, IV et al. |
| 9,326,767 B2 | 5/2016 | Koch, Jr. et al. |
| 9,332,987 B2 | 5/2016 | Leimbach et al. |
| 9,345,477 B2 | 5/2016 | Anim et al. |
| 9,345,478 B2 | 5/2016 | Knodel |
| 9,345,481 B2 | 5/2016 | Hall et al. |
| 9,345,780 B2 | 5/2016 | Manoharan et al. |
| 9,351,727 B2 | 5/2016 | Leimbach et al. |
| 9,351,732 B2 | 5/2016 | Hodgkinson |
| 9,358,003 B2 | 6/2016 | Hall et al. |
| 9,364,217 B2 | 6/2016 | Kostrzewski et al. |
| 9,364,218 B2 | 6/2016 | Scirica |
| 9,364,219 B2 | 6/2016 | Olson et al. |
| 9,364,220 B2 | 6/2016 | Williams |
| 9,364,233 B2 | 6/2016 | Alexander, III et al. |
| 9,370,358 B2 | 6/2016 | Shelton, IV et al. |
| 9,370,362 B2 | 6/2016 | Petty et al. |
| 9,386,983 B2 | 7/2016 | Swensgard et al. |
| 9,386,988 B2 | 7/2016 | Baxter, III et al. |
| 9,393,018 B2 | 7/2016 | Wang et al. |
| 9,398,911 B2 | 7/2016 | Auld |
| 9,402,604 B2 | 8/2016 | Williams et al. |
| 9,421,014 B2 | 8/2016 | Ingmanson et al. |
| 9,433,419 B2 | 9/2016 | Gonzalez et al. |
| 9,433,420 B2 | 9/2016 | Hodgkinson |
| 9,445,810 B2 | 9/2016 | Cappola |
| 9,445,813 B2 | 9/2016 | Shelton, IV et al. |
| 9,451,959 B2 | 9/2016 | Patankar et al. |
| 9,468,438 B2 | 10/2016 | Baber et al. |
| 9,468,439 B2 | 10/2016 | Cappola et al. |
| 9,480,476 B2 | 11/2016 | Aldridge et al. |
| 9,480,492 B2 | 11/2016 | Aranyi et al. |
| 9,492,171 B2 | 11/2016 | Patenaude |
| 9,498,212 B2 | 11/2016 | Racenet et al. |
| 9,510,827 B2 | 12/2016 | Kostrzewski |
| 9,517,065 B2 | 12/2016 | Simms et al. |
| 9,517,066 B2 | 12/2016 | Racenet et al. |
| 9,539,007 B2 | 1/2017 | Dhakad et al. |
| 9,549,735 B2 | 1/2017 | Shelton, IV et al. |
| 9,554,796 B2 | 1/2017 | Kostrzewski |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0112256 A1 | 4/2009 | Boyden et al. |
| 2009/0242610 A1 | 10/2009 | Shelton, IV et al. |
| 2009/0255974 A1 | 10/2009 | Viola |
| 2009/0308907 A1 | 12/2009 | Nalagatla et al. |
| 2010/0012703 A1 | 1/2010 | Calabrese et al. |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |

(56) References Cited

U.S. PATENT DOCUMENTS

| | | |
|---|---|---|
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2011/0006101 A1 | 1/2011 | Hall et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0087276 A1 | 4/2011 | Bedi et al. |
| 2011/0101069 A1 | 5/2011 | Bombard et al. |
| 2011/0114702 A1 | 5/2011 | Farascioni |
| 2011/0121049 A1 | 5/2011 | Malinouskas et al. |
| 2011/0147433 A1 | 6/2011 | Shelton, IV et al. |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0278343 A1 | 11/2011 | Knodel et al. |
| 2011/0290856 A1 | 12/2011 | Shelton, IV et al. |
| 2012/0016362 A1 | 1/2012 | Heinrich et al. |
| 2012/0053406 A1 | 3/2012 | Conlon et al. |
| 2012/0061446 A1 | 3/2012 | Knodel et al. |
| 2012/0074200 A1 | 3/2012 | Schmid et al. |
| 2012/0080478 A1 | 4/2012 | Morgan et al. |
| 2012/0080495 A1 | 4/2012 | Holcomb et al. |
| 2012/0080498 A1 | 4/2012 | Shelton, IV et al. |
| 2012/0091183 A1 | 4/2012 | Manoux et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0234895 A1 | 9/2012 | O'Connor et al. |
| 2012/0234897 A1 | 9/2012 | Shelton, IV et al. |
| 2012/0241492 A1 | 9/2012 | Shelton, IV et al. |
| 2012/0241493 A1 | 9/2012 | Baxter, III et al. |
| 2012/0241504 A1 | 9/2012 | Soltz et al. |
| 2012/0248169 A1 | 10/2012 | Widenhouse et al. |
| 2012/0286021 A1 | 11/2012 | Kostrzewski |
| 2012/0286022 A1 | 11/2012 | Olson et al. |
| 2012/0298722 A1 | 11/2012 | Hess et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037595 A1 | 2/2013 | Gupta et al. |
| 2013/0041406 A1 | 2/2013 | Bear et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0075447 A1 | 3/2013 | Weisenburgh, II et al. |
| 2013/0092717 A1 | 4/2013 | Marczyk et al. |
| 2013/0098964 A1 | 4/2013 | Smith et al. |
| 2013/0098966 A1 | 4/2013 | Kostrzewski et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | (Tarinelli) Racenet et al. |
| 2013/0112730 A1 | 5/2013 | Whitman et al. |
| 2013/0119109 A1 | 5/2013 | Farascioni et al. |
| 2013/0146641 A1 | 6/2013 | Shelton, IV et al. |
| 2013/0146642 A1 | 6/2013 | Shelton, IV et al. |
| 2013/0153636 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0175316 A1 | 7/2013 | Thompson et al. |
| 2013/0193188 A1 | 8/2013 | Shelton, IV et al. |
| 2013/0256380 A1 | 10/2013 | Schmid et al. |
| 2013/0277410 A1 | 10/2013 | Fernandez et al. |
| 2013/0334280 A1 | 12/2013 | Krehel et al. |
| 2014/0014704 A1 | 1/2014 | Onukuri et al. |
| 2014/0014707 A1 | 1/2014 | Onukuri et al. |
| 2014/0021242 A1 | 1/2014 | Hodgkinson et al. |
| 2014/0048580 A1 | 2/2014 | Merchant et al. |
| 2014/0061280 A1 | 3/2014 | Ingmanson et al. |
| 2014/0076955 A1 | 3/2014 | Lorenz |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0166720 A1 | 6/2014 | Chowaniec et al. |
| 2014/0166721 A1 | 6/2014 | Stevenson et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175146 A1 | 6/2014 | Knodel |
| 2014/0175150 A1 | 6/2014 | Shelton, IV et al. |
| 2014/0203062 A1 | 7/2014 | Viola |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239043 A1 | 8/2014 | Simms et al. |
| 2014/0239044 A1 | 8/2014 | Hoffman |
| 2014/0239047 A1 | 8/2014 | Hodgkinson et al. |
| 2014/0246471 A1 | 9/2014 | Jaworek et al. |
| 2014/0246472 A1 | 9/2014 | Kimsey et al. |
| 2014/0246475 A1 | 9/2014 | Hall et al. |
| 2014/0246478 A1 | 9/2014 | Baber et al. |
| 2014/0252062 A1 | 9/2014 | Mozdzierz |
| 2014/0252064 A1 | 9/2014 | Mozdzierz et al. |
| 2014/0252065 A1 | 9/2014 | Hessler et al. |
| 2014/0263539 A1 | 9/2014 | Leimbach et al. |
| 2014/0263540 A1 | 9/2014 | Covach et al. |
| 2014/0263541 A1 | 9/2014 | Leimbach et al. |
| 2014/0263542 A1 | 9/2014 | Leimbach et al. |
| 2014/0263544 A1 | 9/2014 | Ranucci et al. |
| 2014/0263546 A1 | 9/2014 | Aranyi |
| 2014/0263550 A1 | 9/2014 | Aranyi et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263557 A1 | 9/2014 | Schaller |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263570 A1 | 9/2014 | Hopkins |
| 2014/0284371 A1 | 9/2014 | Morgan et al. |
| 2014/0291379 A1 | 10/2014 | Schellin et al. |
| 2014/0291380 A1 | 10/2014 | Weaner et al. |
| 2014/0291383 A1 | 10/2014 | Spivey et al. |
| 2014/0303668 A1 | 10/2014 | Nicholas et al. |
| 2014/0309665 A1 | 10/2014 | Parihar et al. |
| 2014/0332578 A1 | 11/2014 | Fernandez et al. |
| 2014/0339286 A1 | 11/2014 | Motooka et al. |
| 2014/0353358 A1 | 12/2014 | Shelton, IV et al. |
| 2014/0367445 A1 | 12/2014 | Ingmanson et al. |
| 2014/0367446 A1 | 12/2014 | Ingmanson et al. |
| 2015/0031935 A1* | 1/2015 | Wazer ................ A61N 5/1027 600/8 |
| 2015/0048143 A1 | 2/2015 | Scheib et al. |
| 2015/0053740 A1 | 2/2015 | Shelton, IV |
| 2015/0053742 A1 | 2/2015 | Shelton, IV et al. |
| 2015/0053744 A1 | 2/2015 | Swayze et al. |
| 2015/0060517 A1 | 3/2015 | Williams |
| 2015/0076205 A1 | 3/2015 | Zergiebel |
| 2015/0076211 A1 | 3/2015 | Irka et al. |
| 2015/0080912 A1 | 3/2015 | Sapre |
| 2015/0129633 A1 | 5/2015 | Shariati |

(56) References Cited

U.S. PATENT DOCUMENTS

| | | |
|---|---|---|
| 2015/0133996 A1 | 5/2015 | Shelton, IV et al. |
| 2015/0134076 A1 | 5/2015 | Shelton, IV et al. |
| 2015/0150556 A1 | 6/2015 | McCuen |
| 2015/0157321 A1 | 6/2015 | Lergiebel et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173748 A1 | 6/2015 | Marczyk et al. |
| 2015/0173749 A1 | 6/2015 | Shelton, IV et al. |
| 2015/0173750 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0182220 A1 | 7/2015 | Yates et al. |
| 2015/0209040 A1 | 7/2015 | Whitman et al. |
| 2015/0250474 A1 | 9/2015 | Abbott et al. |
| 2015/0297225 A1 | 10/2015 | Huitema et al. |
| 2015/0316431 A1 | 11/2015 | Collins et al. |
| 2015/0351765 A1 | 12/2015 | Valentine et al. |
| 2015/0359534 A1 | 12/2015 | Gibbons, Jr. |
| 2015/0366560 A1 | 12/2015 | Chen et al. |
| 2015/0374371 A1 | 12/2015 | Richard et al. |
| 2015/0374372 A1 | 12/2015 | Zergiebel et al. |
| 2015/0374376 A1 | 12/2015 | Shelton, IV |
| 2016/0030040 A1 | 2/2016 | Calderoni et al. |
| 2016/0051259 A1 | 2/2016 | Hopkins et al. |
| 2016/0058443 A1 | 3/2016 | Yates et al. |
| 2016/0066907 A1 | 3/2016 | Cheney et al. |
| 2016/0067074 A1 | 3/2016 | Thompson et al. |
| 2016/0089137 A1 | 3/2016 | Hess et al. |
| 2016/0095585 A1 | 4/2016 | Zergiebel et al. |
| 2016/0100835 A1 | 4/2016 | Linder et al. |
| 2016/0106406 A1 | 4/2016 | Cabrera et al. |
| 2016/0113647 A1 | 4/2016 | Hodgkinson |
| 2016/0113648 A1 | 4/2016 | Zergiebel et al. |
| 2016/0113649 A1 | 4/2016 | Zergiebel et al. |
| 2016/0120542 A1 | 5/2016 | Westling et al. |
| 2016/0166249 A1 | 6/2016 | Knodel |
| 2016/0166253 A1 | 6/2016 | Knodel |
| 2016/0199064 A1 | 7/2016 | Shelton, IV et al. |
| 2016/0199084 A1 | 7/2016 | Takei |
| 2016/0206315 A1 | 7/2016 | Olson |
| 2016/0206336 A1 | 7/2016 | Frushour |
| 2016/0235494 A1 | 8/2016 | Shelton, IV et al. |
| 2016/0242773 A1 | 8/2016 | Sadowski et al. |
| 2016/0242774 A1 | 8/2016 | Ebner |
| 2016/0242779 A1 | 8/2016 | Aranyi et al. |
| 2016/0249915 A1 | 9/2016 | Beckman et al. |
| 2016/0249916 A1 | 9/2016 | Shelton, IV et al. |
| 2016/0249918 A1 | 9/2016 | Shelton, IV et al. |
| 2016/0249927 A1 | 9/2016 | Beckman et al. |
| 2016/0249929 A1 | 9/2016 | Cappola et al. |
| 2016/0249945 A1 | 9/2016 | Shelton, IV et al. |
| 2016/0256071 A1 | 9/2016 | Shelton, IV et al. |
| 2016/0256152 A1 | 9/2016 | Kostrzewski |
| 2016/0256154 A1 | 9/2016 | Shelton, IV et al. |
| 2016/0256160 A1 | 9/2016 | Shelton, IV et al. |
| 2016/0256161 A1 | 9/2016 | Overmyer et al. |
| 2016/0256162 A1 | 9/2016 | Shelton, IV et al. |
| 2016/0256163 A1 | 9/2016 | Shelton, IV et al. |
| 2016/0256184 A1 | 9/2016 | Shelton, IV et al. |
| 2016/0256185 A1 | 9/2016 | Shelton, IV et al. |
| 2016/0256187 A1 | 9/2016 | Shelton, IV et al. |
| 2016/0262750 A1 | 9/2016 | Hausen et al. |
| 2016/0270783 A1 | 9/2016 | Yigit et al. |
| 2016/0270788 A1 | 9/2016 | Czernik |
| 2016/0278764 A1 | 9/2016 | Shelton, IV et al. |
| 2016/0278765 A1 | 9/2016 | Shelton, IV et al. |
| 2016/0278771 A1 | 9/2016 | Shelton, IV et al. |
| 2016/0278774 A1 | 9/2016 | Shelton, IV et al. |
| 2016/0278775 A1 | 9/2016 | Shelton, IV et al. |
| 2016/0278777 A1 | 9/2016 | Shelton, IV et al. |
| 2016/0278848 A1 | 9/2016 | Boudreaux et al. |
| 2016/0287250 A1 | 10/2016 | Shelton, IV et al. |
| 2016/0287251 A1 | 10/2016 | Shelton, IV et al. |
| 2016/0296216 A1 | 10/2016 | Nicholas et al. |
| 2016/0296226 A1 | 10/2016 | Kostrzewski |
| 2016/0302791 A1 | 10/2016 | Schmitt |
| 2016/0310134 A1 | 10/2016 | Contini et al. |
| 2016/0324514 A1 | 11/2016 | Srinivas et al. |
| 2016/0324518 A1 | 11/2016 | Nicholas et al. |
| 2016/0338703 A1 | 11/2016 | Scirica et al. |
| 2016/0345971 A1 | 12/2016 | Bucciaglia et al. |
| 2016/0345973 A1 | 12/2016 | Marczyk et al. |
| 2016/0354176 A1 | 12/2016 | Schmitt |
| 2016/0361056 A1* | 12/2016 | Wazer .................. A61N 5/1027 |
| 2016/0374678 A1 | 12/2016 | Becerra et al. |
| 2017/0000483 A1 | 1/2017 | Motai et al. |
| 2017/0020525 A1 | 1/2017 | Shah |

FOREIGN PATENT DOCUMENTS

| | | |
|---|---|---|
| CA | 2884962 A1 | 11/2015 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0 760 230 A1 | 3/1997 |
| EP | 1952769 A2 | 8/2008 |
| EP | 2090253 A2 | 8/2009 |
| EP | 2090254 A1 | 8/2009 |
| EP | 2583630 A2 | 4/2013 |
| EP | 2586382 A2 | 5/2013 |
| EP | 2907456 A1 | 8/2015 |
| EP | 3189795 A2 | 7/2017 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |

(56) References Cited

FOREIGN PATENT DOCUMENTS

| | | |
|---|---|---|
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51-149985 | 12/1976 |
| JP | 2001-87272 | 4/2001 |
| SU | 659146 A1 | 4/1979 |
| SU | 728848 A1 | 4/1980 |
| SU | 980703 A1 | 12/1982 |
| SU | 990220 A1 | 1/1983 |
| WO | 08302247 | 7/1983 |
| WO | 89/10094 A1 | 11/1989 |
| WO | 9210976 A1 | 7/1992 |
| WO | 9308754 A | 5/1993 |
| WO | 9314706 A1 | 8/1993 |
| WO | 2004/032760 A2 | 4/2004 |
| WO | 2009071070 A2 | 6/2009 |
| WO | 2011/078519 A2 | 6/2011 |
| WO | 2012/158416 A1 | 11/2012 |
| WO | 20150191887 A1 | 12/2015 |

OTHER PUBLICATIONS

European Office Action issued in Application No. 18150357.4, dated Sep. 24, 2019 (6 pages).

\* cited by examiner

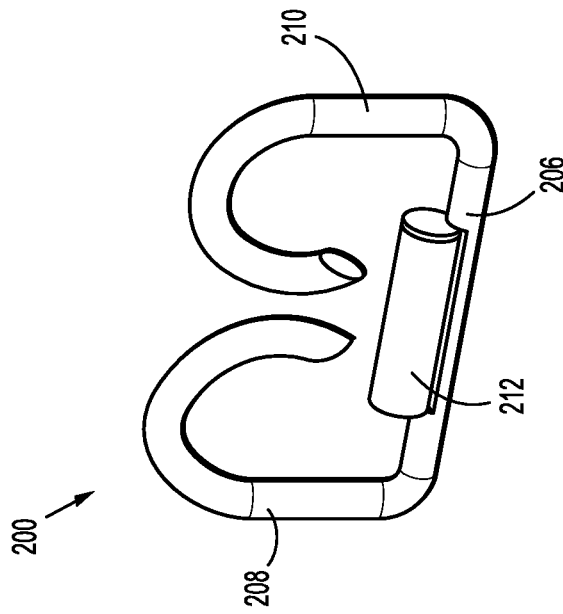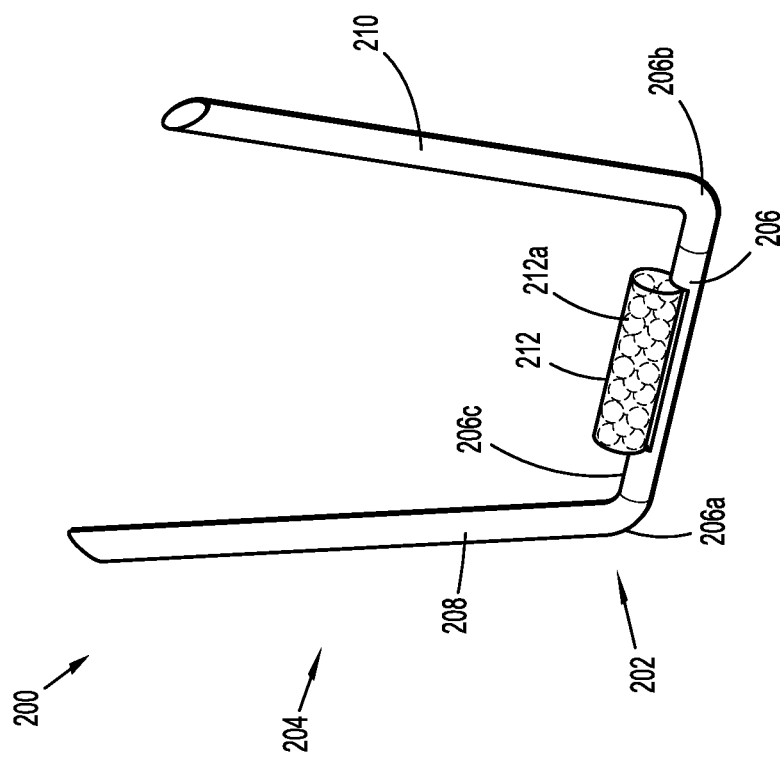

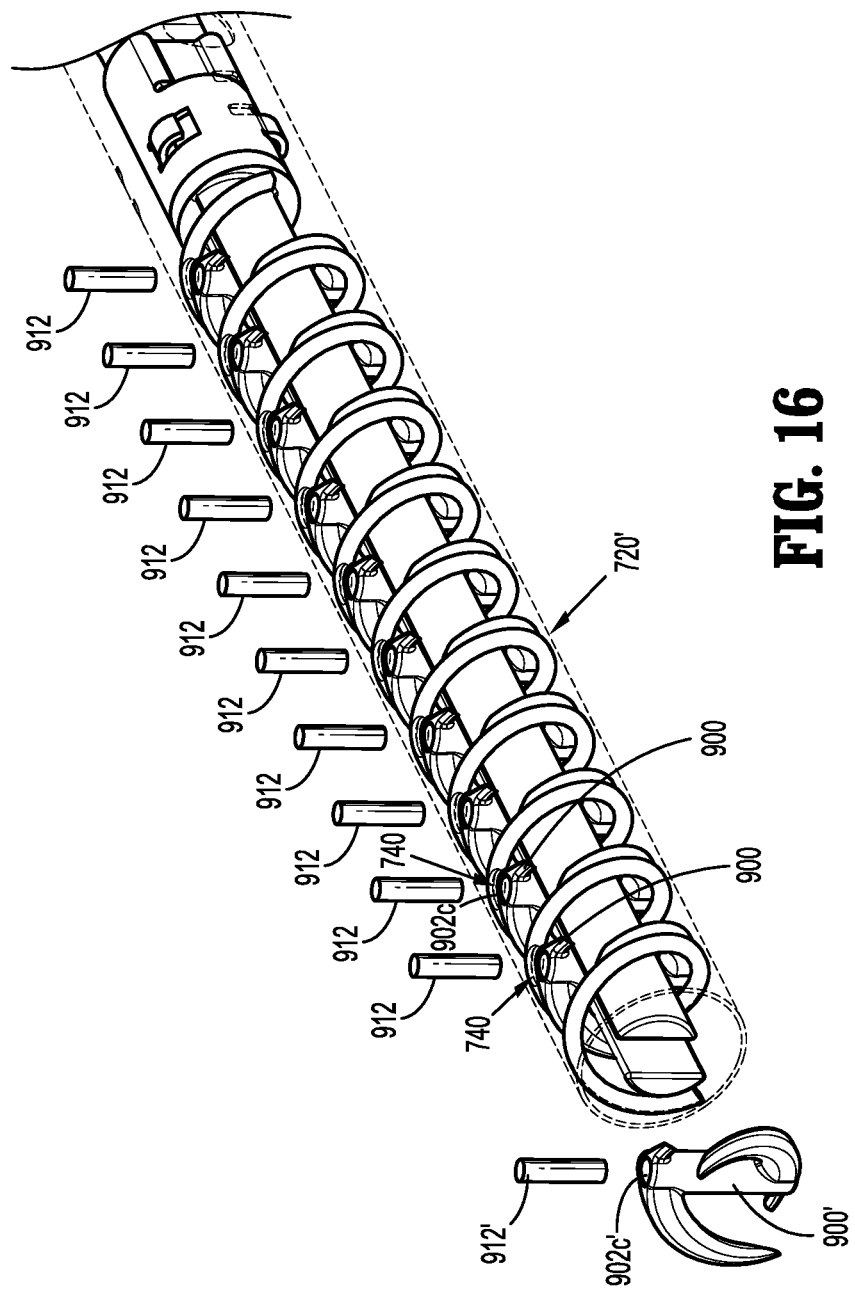

IMPLANTABLE FASTENERS, APPLICATORS, AND METHODS FOR BRACHYTHERAPY

CROSS-REFERENCE TO RELATED APPLICATION

This application claims the benefit of and priority to U.S. Provisional Patent Application No. 62/514,089 filed Jun. 2, 2017, U.S. Provisional Patent Application No. 62/451,936 filed Jan. 30, 2017, U.S. Provisional Patent Application No. 62/442,610 filed Jan. 5, 2017, the entire disclosure of which is incorporated by reference herein.

BACKGROUND

1. Technical Field

The present disclosure relates to surgical implants, staples, clips or fasteners and, more particularly, to implantable fasteners including low dose brachytherapy capsules, and fastener applicators therefor.

2. Background of Related Art

Generally, brachytherapy is an advanced form of cancer treatment. Specifically, radioactive seeds (alone or incorporated within sutures, buttresses or the like) are placed in or near the cancer site itself, where they emit a relatively low dose of radiation directly to the cancer site while reducing exposure of surrounding healthy tissue to the radiation.

Depending on the underlying cancer to be treated and on the underlying tissue, particular dosimetry guidelines have been developed for the placement of radioactive seeds and for the radiation levels emitted by the radioactive seeds. Generally, the radioactive seeds are placed at predefined distances relative to one another in order to enable effective dosimetry.

Accordingly, improved structures incorporating radioactive seeds and methods of placing those structures at or near cancer sites may be advantageous.

SUMMARY

Implantable fasteners having brachytherapy capsules including radioactive seeds are provided in accordance with the present disclosure. The implantable fasteners having brachytherapy capsules are individually placed at a cancer site using fastener applicators in accordance with the present disclosure.

According to an aspect of the present disclosure, a fastener applicator is provided and includes a body portion including a handle assembly, a cartridge assembly supported within the body portion, the cartridge assembly including implantable fasteners, a drive assembly supported within the body portion and operatively coupled to the cartridge assembly to engage the implantable fasteners, and an actuation assembly supported within the handle assembly and operatively coupled to the drive assembly to fire a distal-most implantable fastener upon actuation of the actuation assembly. At least one of the implantable fasteners includes a body including a tissue facing surface, a tissue penetrating portion extending from the body, and a capsule affixed to the tissue facing surface of the body, the capsule including radioactive material.

In certain embodiments, at least one of the implantable fasteners may be a surgical staple and include a radioactive material configured to provide a dose of radiation to a target surgical site.

In some embodiments, the body of at least one of the implantable fasteners includes a backspan having the tissue facing surface, the tissue facing surface defining a flattened surface extending along at least a portion thereof, the flattened surface providing an increased surface area for affixing the capsule onto the tissue facing surface of the backspan.

In embodiments, the tissue penetrating portion of at least one of the implantable fasteners includes a first leg extending from a first end portion of the backspan and a second leg extending from a second end portion of the backspan, wherein the first leg and the second leg extend substantially in a same direction from the backspan.

In certain embodiments, the tissue penetrating portion of at least one of the implantable fasteners includes an unformed condition wherein the first leg and the second leg are substantially parallel to one another and spaced a relative distance from one another, and a formed condition wherein the first leg and the second leg are radiused and in relative close approximation to one another and the backspan.

In some embodiments, radioactive material is dispersed throughout at least one of the implantable fasteners such that the entirety of at least one of the implantable fasteners emits radiation.

In embodiments, the implantable fasteners includes a first implantable fastener having sufficient mechanical strength to hold tissue together, and a second implantable fastener having the capsule affixed thereon for providing the dose of radiation to the target surgical site.

In certain embodiments, each of the first leg and the second leg of the surgical staple includes a first portion and a second portion, the first portion of the first leg and the first portion of the second leg extending away from the backspan at an angle such that the first portions of the first leg and the second leg overlap, the second portions of the first leg and the second leg extending from the first portions of each of the first leg and the second leg, respectively, towards the backspan.

According to another aspect of the present disclosure, a method of performing a surgical procedure at a surgical site includes positioning a fastener applicator within an opening in tissue, the fastener applicator loaded with implantable fasteners, each implantable fastener having a body including a tissue facing surface, a tissue penetrating portion extending from the body, and a capsule affixed to the tissue facing surface of the body, the capsule including radioactive material. The method further includes locating a first target of the surgical site, and firing the fastener applicator to secure a first implantable fastener to the first target of the surgical site such that the capsule affixed thereon is in contact with tissue adjacent the first target of the surgical site.

In embodiments, the method further includes locating a second target of the surgical site, relocating the fastener applicator to the second target of the surgical site, and firing the fastener applicator to secure a second implantable fastener to the second target such that the capsule affixed thereon is in contact with tissue adjacent the second target of the surgical site.

In certain embodiments, the method further includes locating a plurality of targets of the surgical site, relocating the fastener applicator to the plurality of targets of the surgical site, and arranging the implantable fasteners in any configuration, in any pattern, or in any quantity.

BRIEF DESCRIPTION OF THE DRAWINGS

The present disclosure will be further described with reference to the accompanying drawings, wherein like reference numerals refer to like parts in the several views, and wherein:

FIG. 3A is a perspective view of an implantable fastener in accordance with another embodiment of the present disclosure in an unformed condition;

FIG. 3B is a perspective view of the implantable fastener of FIG. 3A in a formed condition;

FIG. 16 is a perspective view of another embodiment of a cartridge assembly of the fastener applicator of FIG. 15 for loading the implantable fastener of FIG. 8.

DETAILED DESCRIPTION OF EMBODIMENTS

Figure 1A:
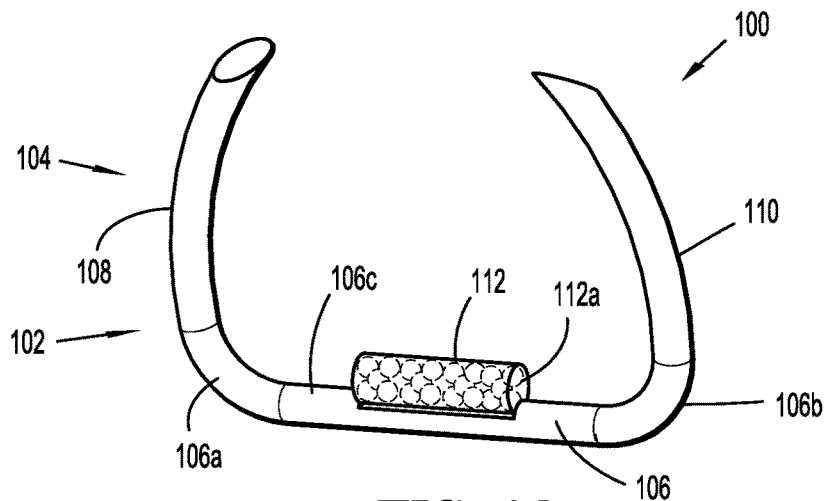
FIG. 1A is a perspective view of an implantable fastener in accordance with an embodiment of the present disclosure in an unformed condition.

Embodiments of the presently disclosed implantable fasteners and fastener applicators will now be described in detail with reference to the drawings, in which like reference numerals designate identical or corresponding elements in each of the several views. In the drawings and in the description that follows, the term "proximal" will refer to the end of the implantable fasteners and fastener applicator which are closest to the operator, while the term "distal" will refer to the end of the implantable fasteners and fastener applicator which are farthest from the operator.

Figure 1B:
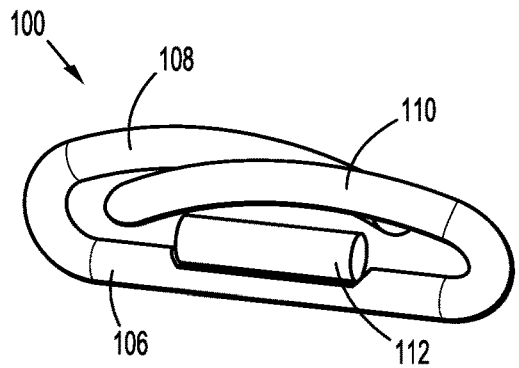
FIG. 1B is a perspective view of the implantable fastener of FIG. 1A in a formed condition.
Figure 1C:
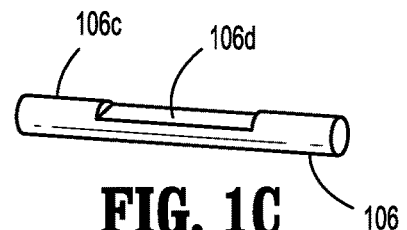
FIG. 1C is a perspective view of a backspan of the implantable fastener of FIG. 1A, illustrating a tissue facing surface thereof.

In accordance with the present disclosure, as illustrated in FIGS. 1A-1C, an embodiment of an implantable fastener 100 is provided and generally includes a body 102 and a tissue penetrating portion 104 extending from the body 102. The body 102 includes a crown or backspan 106 and the tissue penetrating portion 104 includes a first leg 108 extending from a first end portion 106a of the backspan 106 and a second leg 110 extending from a second end portion 106b of the backspan 106. The first leg 108 and the second leg 110 may extend in a same direction such as, for example, distally from the backspan 106.

Figure 2A:
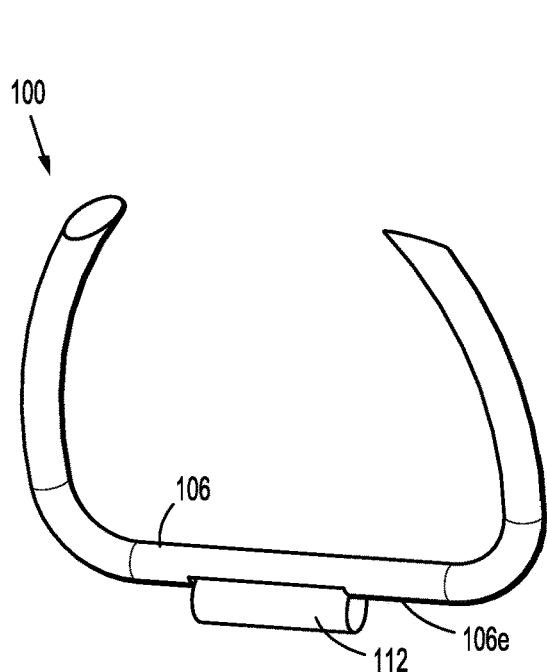
FIGS. 2A-2B are perspective views of the implantable fastener of FIG. 1A, illustrating a capsule affixed thereon at various locations of the backspan.
Figure 2B:
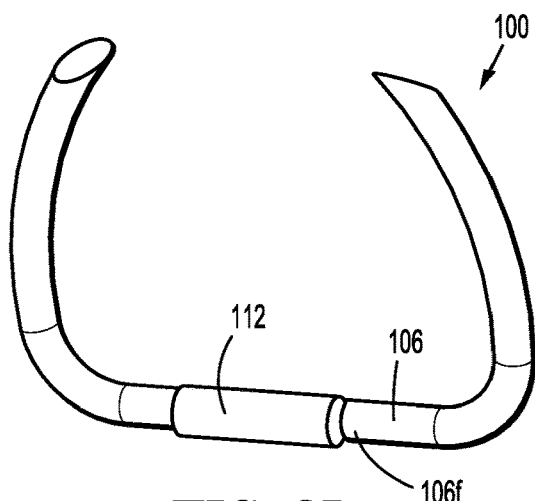

The backspan 106 includes a top or tissue facing surface 106c configured for fixedly supporting a capsule 112 thereon. It is envisioned that capsule 112 includes a radiation source, as will be detailed below. The capsule 112 is affixed to the tissue facing surface 106c of the backspan 106 using laser welding or other suitable methods. In some embodiments, as illustrated in FIG. 1C, the tissue facing surface 106c may include a flattened surface 106d extending along at least a portion thereof and configured to provide an increased surface area for affixing the capsule 112 thereon. In embodiments, the capsule 112 may be affixed to a portion of the backspan 106, such as, for example, the flattened surface 106d of the tissue facing surface 106c, using a snap-fit engagement. The backspan 106 may then be heated or crimped to reduce the probability of the dislocation and migration of capsule 112 from implantable fastener 100. It is contemplated that affixing the capsule 112 on the tissue facing surface 106c of the backspan 106 may be advantageous since it enables the capsule 112 to be in direct contact with a target surgical site, such as, for example, tissue or the like (see FIG. 13). For example, it is contemplated that direct contact between capsule 112 and the target surgical site may provide a controlled, homogeneous dosing of radiation to the target surgical site, while avoiding substantial dosing of normal surrounding structures. It is further contemplated that direct contact between capsule 112 and the target surgical site may provide reduced attenuation of dosing from the radiation source to the target surgical site. Alternatively, as shown in FIGS. 2A and 2B, the capsule 112 may be affixed to a bottom surface 106e or a lateral surface 106f of the backspan 106. Though not specifically shown in the figures, it is contemplated that the first leg 108, the second leg 110 may be affixed directly onto the capsule 112 using laser welding, crimping, or other suitable methods.

Implantable fastener 100 may have an unformed condition, as shown in FIG. 1A, wherein the first leg 108 and the second leg 110 are parallel, or substantially parallel, to one another and spaced a relative distance from one another. Implantable fastener 100 may have a formed condition, as shown in FIG. 1B, wherein the first leg 108 and the second leg 110 are radiused and in relative close approximation to one another and backspan 106.

Implantable fastener 100 may be fabricated from a formable material, such as, for example, titanium, stainless steel or polymers. In this manner, implantable fastener 100 may be introduced over a target vessel or tissue while in an unformed condition, and then formed or fastened onto the target vessel or tissue to secure the implantable fastener 100 to the target vessel or tissue. It is contemplated that implantable fasteners 100 may be fabricated from any non-degradable, biocompatible material known by those having skill in the art. It is further contemplated that the implantable fasteners 100, or any parts thereof, may be formed from a degradable material such as magnesium.

In accordance with the present disclosure, as illustrated in FIGS. 1A-2B, and noted above, implantable fastener 100 may include the capsule 112 having a radiation source. Capsule 112 may be a brachytherapy capsule or seed and include a radioactive material 112a disposed therein. The radioactive material 112a may include any of a number of radioactive isotopes. Possible low dose isotopes include, but are not limited to, Cesium-131 ($^{131}$Cs), Iridium-192 ($^{192}$Ir), Iodine-125 ($^{125}$I), Palladium-103 ($^{103}$Pd), and Ytterbium-169 ($^{169}$Yb). Therapeutic dosages may range from 80 to 150 Gy depending on the isotope and desired exposure. Implantable fastener 100 may have various target energies to provide flexibility in planning the treatment. It is envisioned that a particular strength of the radiation field and/or a particular geometry of the radiation field may be a function of the radioactive material 112a. It is further envisioned that capsule 112 may be dimensioned so as to determine the geometry of the emitted radiation or the strength of the emitted radiation. It is contemplated that a length of capsule 112 may be less than a length of backspan 106 so as to not interfere with the formation of implantable fastener 100.

Though not specifically shown in the figures, it is contemplated that the first leg 108, the second leg 110, and/or backspan 106 may include one or more cavities for receiving capsules 112 or radioactive material 112a. Any other combinations of placement of capsule 112, as well as integration of capsule 112 in implantable fastener 100 is also contemplated and within the scope of the present disclosure.

It is further envisioned, that implantable fastener 100 may be processed such that the entirety of implantable fastener 100 emits radiation from radioactive material 112a dispersed throughout implantable fastener 100. For example, and within the purview of the present disclosure, implantable fastener 100 may be processed so as to determine the strength of the emitted radiation. Specifically, in an embodiment, implantable fastener 100 may be a polymeric surgical clip fabricated from a radioactive biocompatible material.

It is contemplated that implantable fasteners 100 having radioactive material 112a disposed therein may be locatable using imaging techniques, such as, for example, X-ray or the like. In embodiments where implantable fasteners 100 do not include radioactive material 112a, implantable fasteners 100 may be coated with a material, such as, for example, gold, or coated with a colored oxide layer to make implantable fasteners 100 relatively more visible. Gold coatings or other coatings may be utilized to enable radiographic location of implantable fasteners 100 during follow-up procedures. In this manner, implantable fasteners 100 may serve as fiduciary markers.

In accordance with the present disclosure, by fastening the implantable fastener 100 onto a target vessel or tissue, a therapeutic dose of radiation can be applied to a set location and known volume of tissue based on the activity and isotope material of the capsule 112.

In embodiments, implantable fasteners 100 including the capsule 112 serve the purpose of applying a local therapeutic dose of radiation to, for example, a tumor or to a resection site after removal of a cancerous tumor. As such, those implantable fasteners 100 that include the capsule 112 only require sufficient mechanical strength to secure the capsule 112 in place and may not be intended to hold tissue together. However, the plurality of implantable fasteners 100 may include one or more implantable fasteners 100 that are designed with sufficient mechanical strength to hold tissue together. Alternatively, implantable fasteners 100 including the capsule 112 may be designed with sufficient mechanical strength to hold tissue together while also securing the capsule 112 in place.

Implantable fasteners 100 may be applied or fastened to any number of tissues having a tumorous growth or suspected of including cancer cells, such as, for example lung tissue, solid organs, gastro-intestinal tissue, and soft tissues.

In accordance with the present disclosure, it is envisioned that implantable fasteners 100 may be applied separately, and individually, at a predetermined location by a clinician. It is contemplated that capsule 112 has a set three-dimensional field of known radiation strength and geometry, as such, multiple implantable fasteners 100 including capsule 112 may be applied to the target tissue to provide a controlled, homogeneous dosing of the radiation source to the target surgical site.

It is contemplated that implantable fasteners 100 may be applied or arranged in any configuration, pattern, or quantity to achieve the intended purpose. For example, implantable fasteners 100 may be arranged in, for example, a straight line, arcuate, triangular, rectangular, circular or other configuration. It is further contemplated that implantable fasteners 100 may be fastened to the target tissue a uniform distance from one another, to achieve the desired dosimetry. Alternatively, implantable fasteners 100 may be fastened to the target tissue at various distances from one another, or a combination thereof.

In accordance with the present disclosure, while an implantable fastener in the form of implantable fastener 100 has been shown and described in detail, it is contemplated that the implantable fastener may include, and is not limited to, a surgical staple, a surgical coil or the like. As mentioned above, and as contemplated herein, any of the implantable fasteners may be fabricated from a biocompatible material, such as, for example, titanium, stainless steel or polymers. Likewise, as mentioned above, and as contemplated herein, any of the implantable fasteners may incorporate therein or support thereon a capsule 112 having radioactive material 112a, or may be processed such that the entirety of the implantable fastener emits radiation.

For example, with reference to FIGS. 3A and 3B, an implantable fastener in the form of a "B-shaped" surgical staple is shown and generally designated as 200. Similar to implantable fastener 100, implantable fastener 200 may generally include a body 202 and a tissue penetrating portion 204 extending from the body 202. The body 202 includes a crown or backspan 206 and the tissue penetrating portion 204 includes a first leg 208 extending from a first end portion 206a of the backspan 206 and a second leg 210 extending from a second end portion 206b of the backspan 206.

In accordance with the present disclosure, at least one capsule 212, similar to capsule 112, may be affixed to a tissue facing surface 206c of backspan 206. Capsule 212 may include a radioactive material 212a. Additionally or alternatively, it is further envisioned that implantable fastener 200 may be processed such that the entirety of implantable fastener 200 emits radiation from radioactive material dispersed throughout implantable fastener 200. For example, implantable fastener 200 may be processed so as to determine the strength of the emitted radiation.

Implantable fastener 200 may have an unformed condition, as shown in FIG. 3A, wherein the first leg 208 and the second leg 210 are parallel, or substantially parallel, to one another and spaced a relative distance from one another. Implantable fastener 200 may have a formed condition, as shown in FIG. 3B, wherein at least a portion of the first leg 208 and the second leg 210 are radiused and in relative close approximation to one another and backspan 206 to define a substantially B-shaped structure.

Implantable fastener 200 may be fabricated from, for example, titanium, stainless steel or polymers. In an embodiment, implantable fastener 200 may be a polymeric surgical pin fabricated from a radioactive biocompatible material. Some examples of non-degradable biocompatible polymers include polyolefins such as polyethylenes and polypropylenes, nylons, polyesters, silicones, polyimides, polymethylmethacrylates, polyphthalamides, polyurethanes, PTFE, polyethersulfone, polysulfone, PEEK, to name a few.

Figures 4A, 4B:
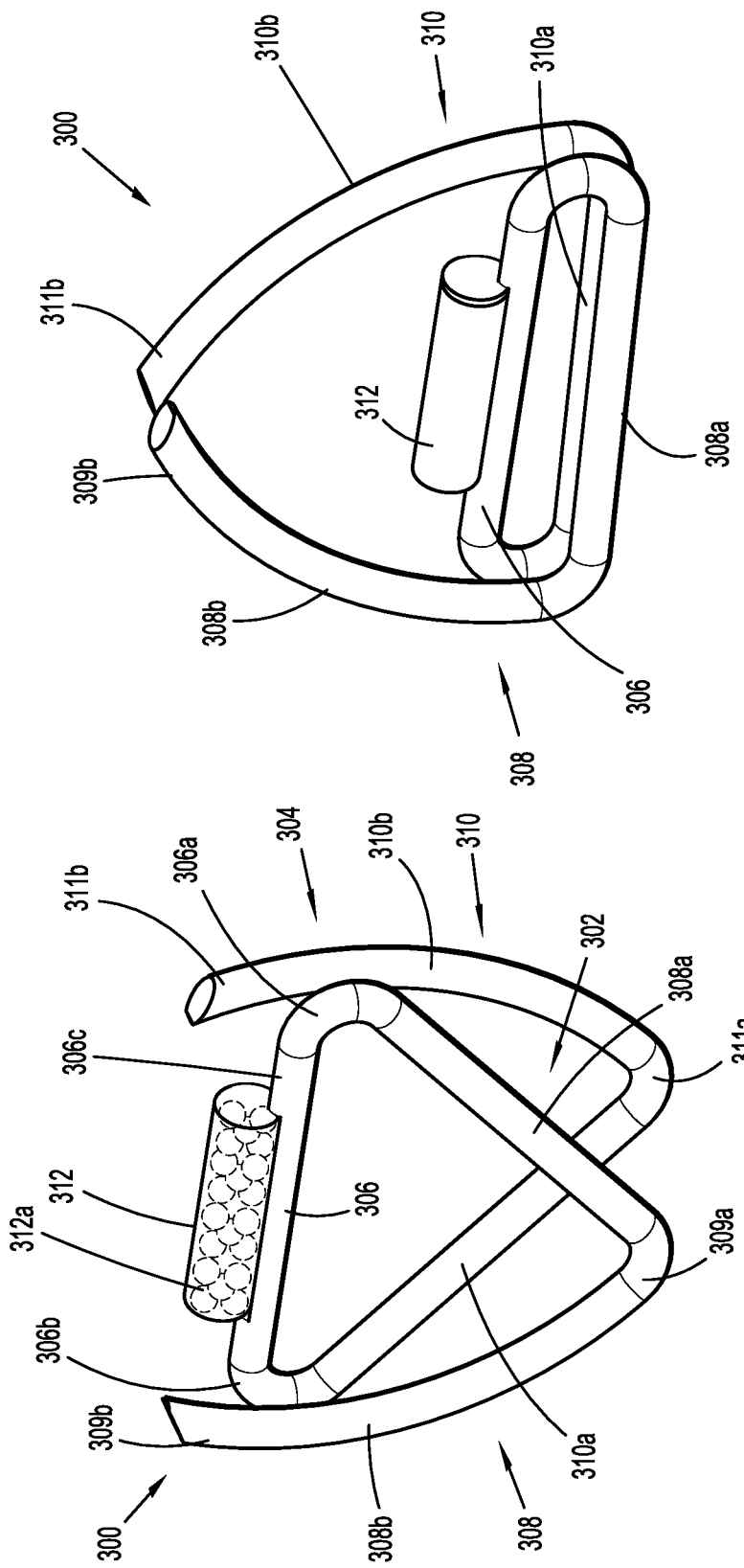
FIG. 4A is a perspective view of an implantable fastener in accordance with another embodiment of the present disclosure in an unformed condition.
FIG. 4B is a perspective view of the implantable fastener of FIG. 4A in a formed condition.

As an additional example, with reference to FIGS. 4A and 4B, an implantable fastener in the form of a "W-shaped" surgical staple is shown and generally designated as 300. Similar to implantable fasteners 100, 200, implantable fastener 300 may generally include a body 302 and a tissue penetrating portion 304 extending from the body 302. The body 302 includes a crown or backspan 306 and the tissue penetrating portion 304 includes a first leg 308 having a first portion 308a and a second portion 308b, and a second leg 310 having a first portion 310a and a second portion 310b. The first portion 308a of the first leg 308 extends from a first end portion 306a of backspan 306 and is coupled to a proximal end portion 309a of the second portion 308b of the first leg 308. Similarly, the first portion 310a of the second leg 310 extends from a second end portion 306b of backspan 306 and is coupled to a proximal end portion 311a of the second portion 3010b of the second leg 310.

In accordance with the present disclosure, at least one capsule 312, similar to capsules 112, 212, may be affixed to a tissue facing surface 306c of backspan 306. Capsule 312 may include a radioactive material 312a. Additionally or alternatively, it is further envisioned that implantable fastener 300 may be processed such that the entirety of implantable fastener 300 emits radiation from radioactive material dispersed throughout implantable fastener 300. It is contemplated that, implantable fastener 300 may be processed so as to determine the strength of the emitted radiation.

In an unformed condition, as shown in FIG. 4A, the backspan 306 is in a distal position relative to the proximal end portions 309a, 311a of the first and second legs 308, 310, respectively. Specifically, backspan 306 is in relative close proximity to a distal end portion 309b of the second portion 308b of the first leg 308 and a distal end portion 311b of the second portion 310b of the second leg 310. In the unformed condition, the first portions 308a, 310a of the first and second legs 308, 310, respectively, extend away from the backspan 306 at an angle such that the first portions 308a, 310a overlap one another, as shown in FIG. 4A. Further, in the unformed condition, the second portions 308b, 310b of the first and second legs 308, 310, respectively, are spaced a relative distance from one another and extend towards backspan 306.

In accordance with the present disclosure, implantable fastener 300 may have a formed condition, as shown in FIG. 4B, wherein the backspan 306 is in a proximal position relative to the distal end portions 309b, 311b of the first and second legs 308, 310, respectively. In the formed condition, at least a portion of the second portions 308b, 310b of the first and second legs 308, 310, respectively, are radiused and in relative close approximation to one another. In the formed condition, as shown in FIG. 4B, the first portions 308a, 310a of the first and second legs 308, 310, respectively, and the backspan 306 are parallel, or substantially parallel, to one another and, and in relative close approximation to one another and backspan 306. Further, in the formed condition, the backspan 306 is spaced a relative distance from the distal end portions 309b,311b of the second portions 308b, 310b of the first and second legs 308, 310, respectively.

Figure 5:
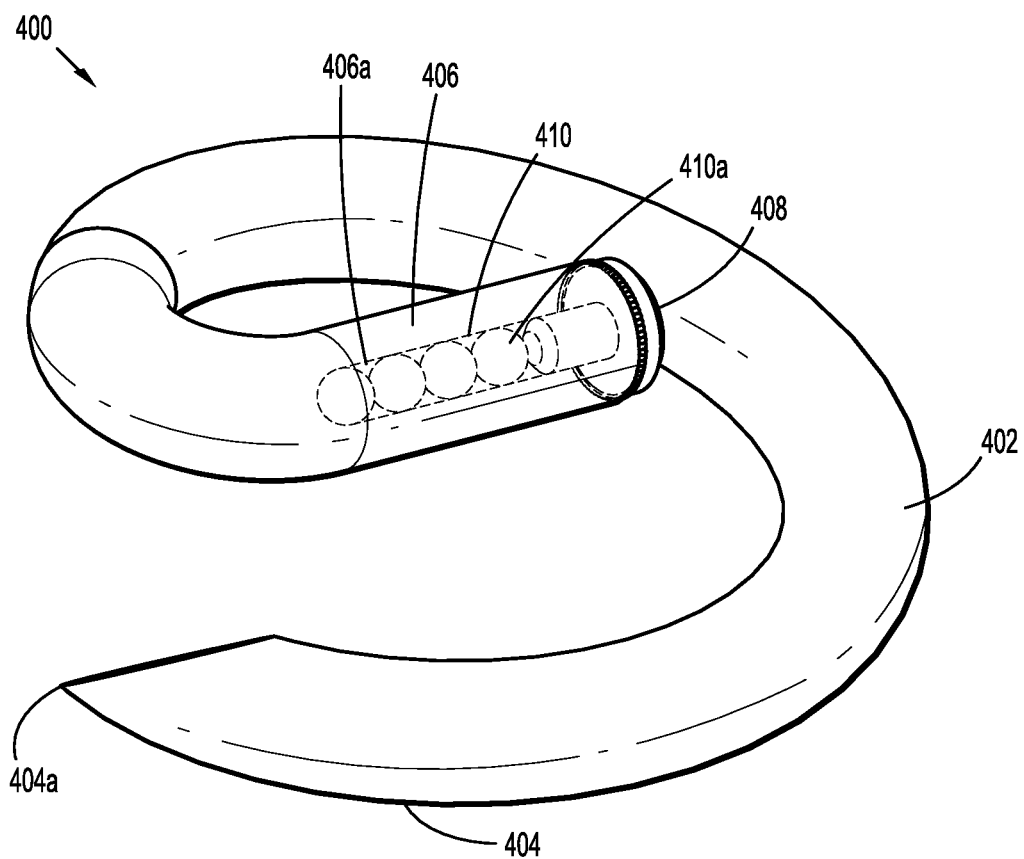
FIG. 5 is a perspective view of an implantable fastener in accordance with another embodiment of the present disclosure.

As an additional example, with reference to FIG. 5, an implantable fastener in the form of a surgical coil is shown and generally designated as 400. Specifically, implantable fastener 400 is a helical-shaped coil fastener. Implantable fastener 400 is designed for application to tissue by rotating implantable fastener 400 into and through the target tissue. Implantable fastener 400 generally includes a coil body portion 402 terminating in a tissue penetrating portion 404. The tissue penetrating portion 404 includes a penetrating point 404a. It is contemplated that the coil body portion 402 may include one or more turns or coils.

Implantable fastener 400 includes a tang 406 at an opposite end of coil body portion 402 from tissue penetrating portion 404. Tang 406 extends generally inwardly toward the center of coil body portion 402 and includes a cavity 406a defined therein. The cavity 406a is capped or closed with a plug 408 having a size and shape corresponding to a size and shape of an opening of the cavity 406a of tang 406.

In accordance with the present disclosure, at least one capsule 410 may be disposed within cavity 406a of tang 406. Similar to capsules 112, 212, 312, capsule 410 includes a radioactive material 410a. Additionally or alternatively, the radioactive material 410a may be disposed within or onto coil body portion 402 of implantable fastener 400. It is further envisioned that implantable fastener 400 may be processed such that the entirety of implantable fastener 400 emits radiation from radioactive material 410a dispersed throughout implantable fastener 400. For example, and within the purview of the present disclosure, implantable fastener 400 may be processed so as to determine the strength of the emitted radiation.

Figure 6:
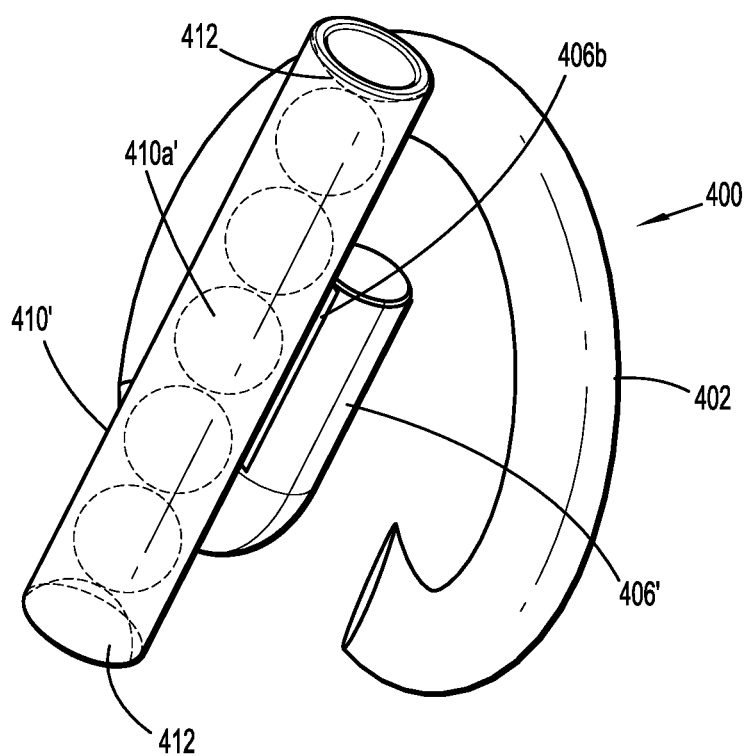
FIG. 6 is a perspective view of an implantable fastener in accordance with another embodiment of the present disclosure.

With reference to FIG. 6, in embodiments, implantable fastener 400 may include at least one capsule 410' affixed to an outer surface of tang 406' using laser welding or other suitable methods. Specifically, tang 406' may include a flattened surface 406b extending along at least a portion thereof and configured to provide an increased surface area for affixing the capsule 410'. Additionally or alternatively, the at least one capsule 410' may be affixed to an outer surface of the coil body portion 402. Similar to capsules 112, 212, 312, 410, capsule 410' includes a radioactive material 410a' disposed therein. Capsule 410' is capped or closed with a plug 412 having a size and shape corresponding to a size and shape of an opening of the capsule 410'. In embodiments, plug 412 is an inverted cap affixed to opposite ends of capsule 410' using laser welding, adhesives, or other suitable methods. Alternatively, plug 412 may include any suitable configuration configured to retain the radioactive material 410a' disposed within the at least one capsule 410'.

Figure 7:
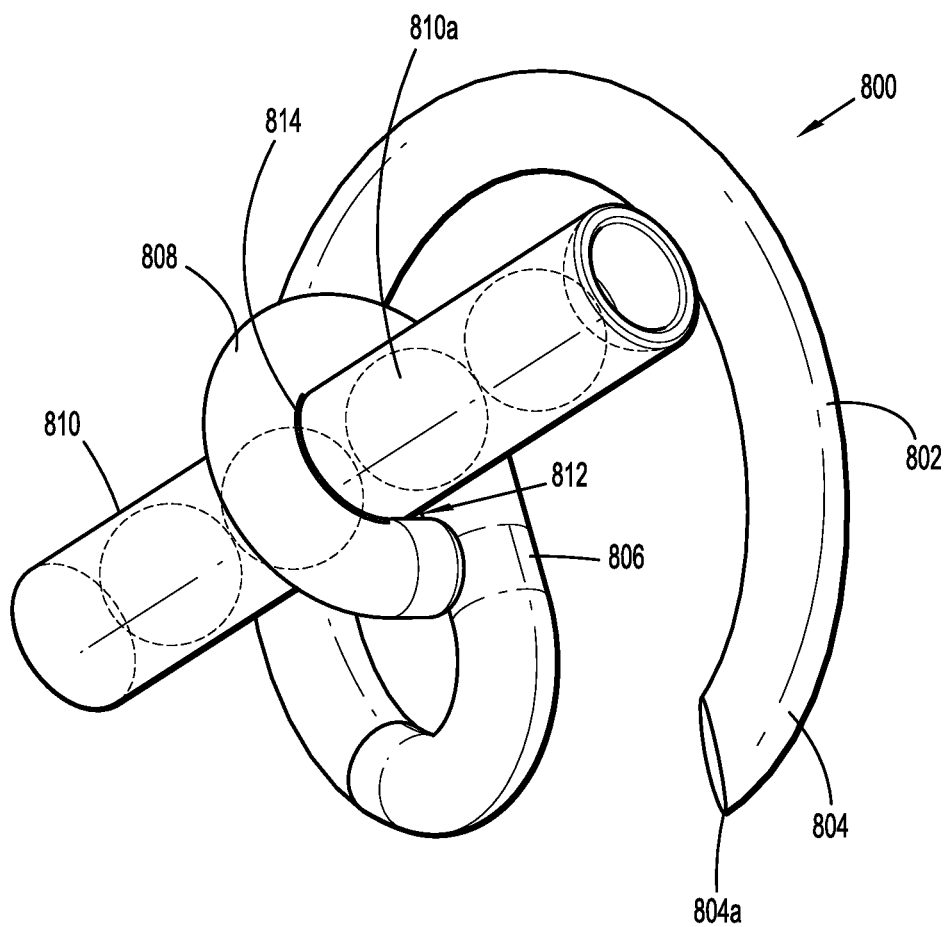
FIG. 7 is a perspective view of an implantable fastener in accordance with another embodiment of the present disclosure.

In embodiments, an implantable fastener 800 is provided as illustrated in FIG. 7. Implantable fastener 800 is a helical-shaped coil fastener similar to the implantable fastener 400 illustrated in FIGS. 5 and 6. Accordingly, implantable fastener 800 generally includes a coil body portion 802 terminating in a tissue penetrating portion 804. The tissue penetrating portion 804 includes a penetrating point 804a. It is contemplated that the coil body portion 802 may include one or more turns or coils.

Implantable fastener 800 includes a tang 806 at an opposite end of coil body portion 802 from tissue penetrating portion 804. Tang 806 extends generally inwardly toward the center of coil body portion 802 and includes a crimped portion 808 configured to capture and retain at least one capsule 810 within a cavity 812 adjacent tang 806. In embodiments, the capsule 810 may be disposed adjacent tang 806 and the crimped portion 808 formed thereabout to secure the capsule 810 within cavity 812 via a friction fit engagement between the tang 806 and the crimped portion 808. Alternatively, the crimped portion 808 may be formed about tang 806 to define cavity 812 and the capsule 810 may be disposed therein. Additionally or alternatively, the capsule 810 may be secured within cavity 812 using laser welding or other suitable methods. In embodiments, at least one of the crimped portion 808 and the tang 806 may include a groove 814 extending along at least a portion thereof and configured to provide an increased surface area for affixing the capsule 810. Capsule 810 is similar to capsule 410' and is configured to retain a radioactive material 810*a* disposed therein.

Implantable fasteners 400, 800 may be fabricated from, for example, titanium, stainless steel or polymers. In an embodiment, implantable fasteners 400, 800 may be a polymeric surgical coil fabricated from a radioactive biocompatible material.

Figure 8:
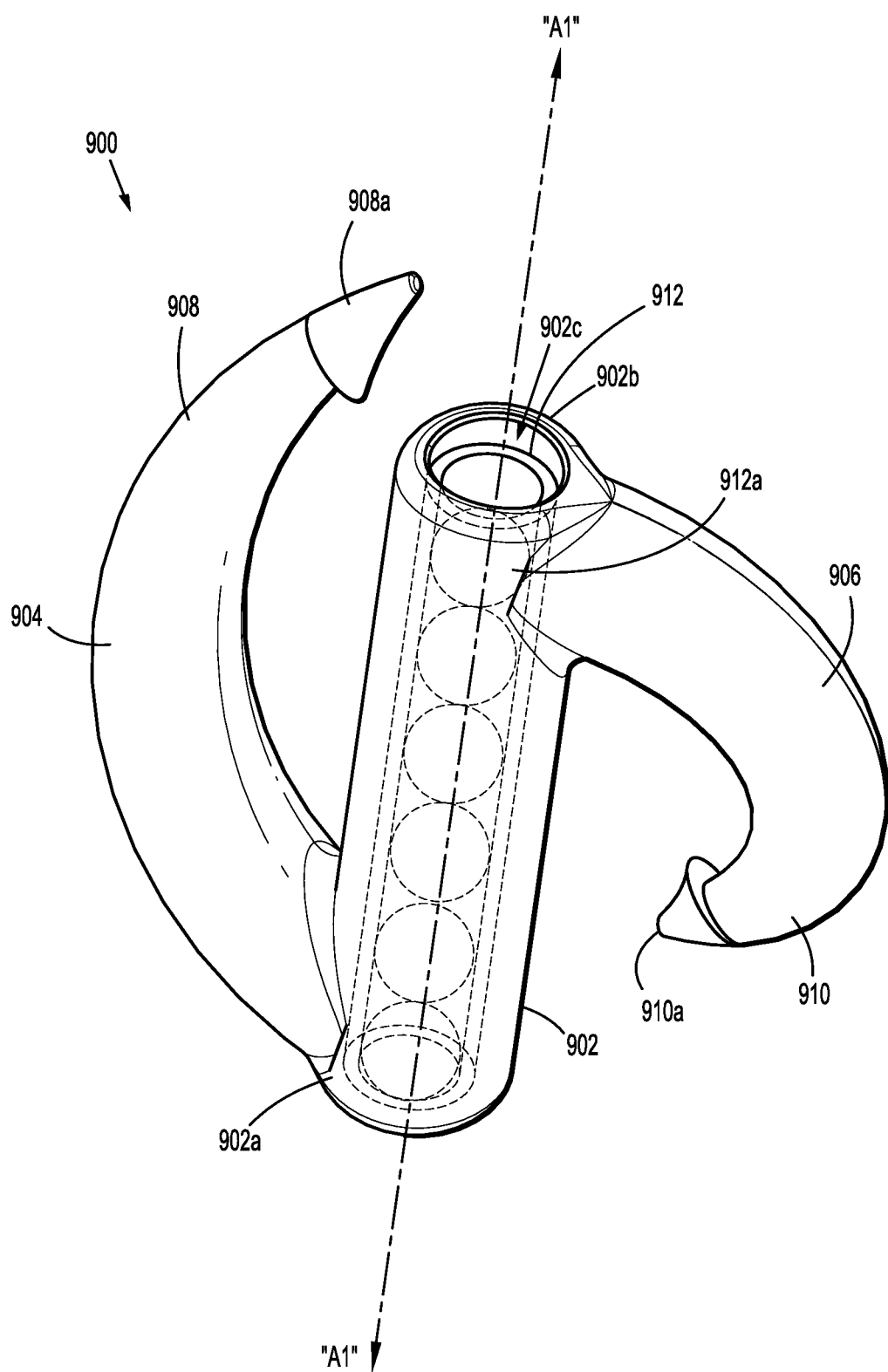
FIG. 8 is a perspective view of an implantable fastener in accordance with another embodiment of the present disclosure.

With reference to FIG. 8, an implantable fastener in the form of an "S-shaped" fastener is shown and generally designated as 900. Implantable fastener 900 generally includes a body 902, a first leg 904, and a second leg 906. Body 902 defines a longitudinal axis "A1-A1" and includes a first end portion 902*a*, an opposing second end portion 902*b*, and a cannula 902*c* extending longitudinally therebetween.

The first leg 904 includes a first tissue penetrating portion 908 having a first tissue penetrating tip 908*a* and the second leg 906 includes a second tissue penetrating portion 910 having a second tissue penetrating tip 910*a*. The first leg 904 extends generally from the first end portion 902*a* of body 902 and radially towards the second end portion 902*b* of body 902 such that the first tissue penetrating tip 908*a* is disposed adjacent the second end portion 902*b* of body 902. Similarly, second leg 906 extends generally from the second end portion 902*b* of body 902 and radially towards the first end portion 902*a* of body 902 such that the second tissue penetrating tip 910*a* is disposed adjacent the first end portion 902*a* of body 902. It is contemplated that the first and second tissue penetrating tips 908*a*, 910*a* may be disposed on either the same lateral side of longitudinal axis "A1-A1", as shown in FIG. 8, or on opposing lateral sides of longitudinal axis "A1-A1".

In accordance with the present disclosure, at least one capsule 912 may be disposed within cannula 902*c* of body 902 and secured therein via a press fit engagement, a friction fit engagement, or other suitable methods. Capsule 912 is similar to capsules 410', 810 and is configured to retain a radioactive material 912*a* disposed therein. With brief reference to FIG. 16, in embodiments, capsule 912' is disposed within cannula 902*c'* of implantable fastener 900' before the implantable fastener 900' is loaded into a cartridge assembly 720'. Alternatively, capsule 912 may be disposed within cannula 902*c* of body 902 after the implantable fastener 900 is loaded into the cartridge assembly, as will be detailed below.

Implantable fastener 900 may be fabricated from, for example, titanium, stainless steel or polymers. In embodiments, the polymer may include a biodegradable polymer with an approximately four to five week in vivo strength retention profile.

While implantable fasteners in the form of a surgical staple and, a surgical coil or the like, have been illustrated and described herein, it is within the scope of the present disclosure that the implantable fasteners may also include two-part fasteners, tacks, locking hinged fasteners, staples or the like. For example, in one embodiment, the implantable fastener may include a two-part polymeric fastener having a coating of polymeric and/or radioactive material.

Figure 9:
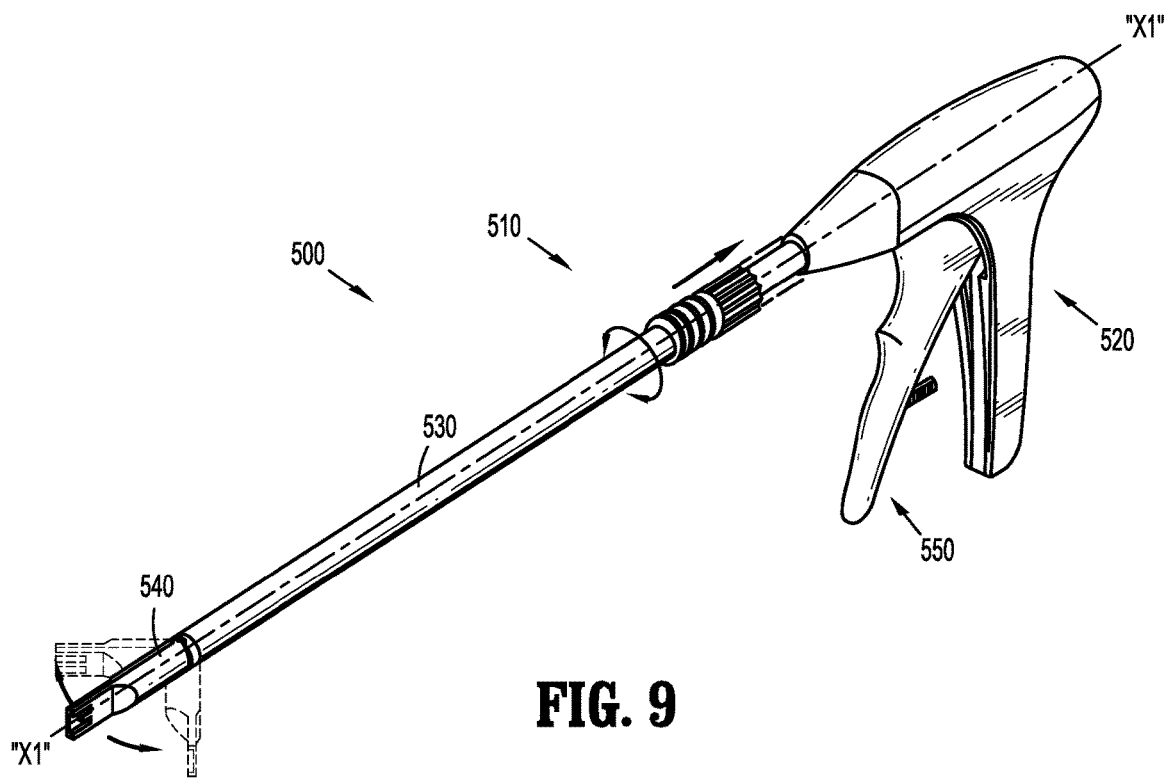
FIG. 9 is a perspective view of a fastener applicator in accordance with an embodiment of the present disclosure, for applying the implantable fasteners of FIGS. 1A-2B.

In order to place implantable fasteners 100 disclosed herein, in accordance with the present disclosure, as illustrated in FIG. 9, a surgical apparatus in the form of a fastener applicator 500 is provided. For a more detailed description of the construction and operation of an example of fastener applicator 500, reference may be made to U.S. Pat. No. 7,624,903, the entire content of which is incorporated herein by reference.

Fastener applicator 500 includes a body portion 510 having a handle assembly 520, an endoscopic shaft assembly 530 extending from handle assembly 520, a cartridge assembly 540 extending from endoscopic shaft assembly 530, and an actuation assembly 550 at least partially supported within the handle assembly 520.

Endoscopic shaft assembly 530 is rotatably connected to handle assembly 520 such that endoscopic shaft assembly 530 is rotatable about a longitudinal axis "X1-X1" thereof. Cartridge assembly 540 is pivotably connected to a distal end portion of endoscopic shaft assembly 530 and is pivotable relative to the longitudinal axis "X1-X1" of endoscopic shaft assembly 530. In FIG. 9, cartridge assembly 540 is shown in general alignment with the longitudinal axis "X1-X1" of endoscopic shaft assembly 530 and additionally in phantom to illustrate a range of movement or articulation. The total range of pivotal motion of cartridge assembly 540 as shown is approximately 90 degrees, i.e. 45 degrees to each side of neutral.

Figure 10:
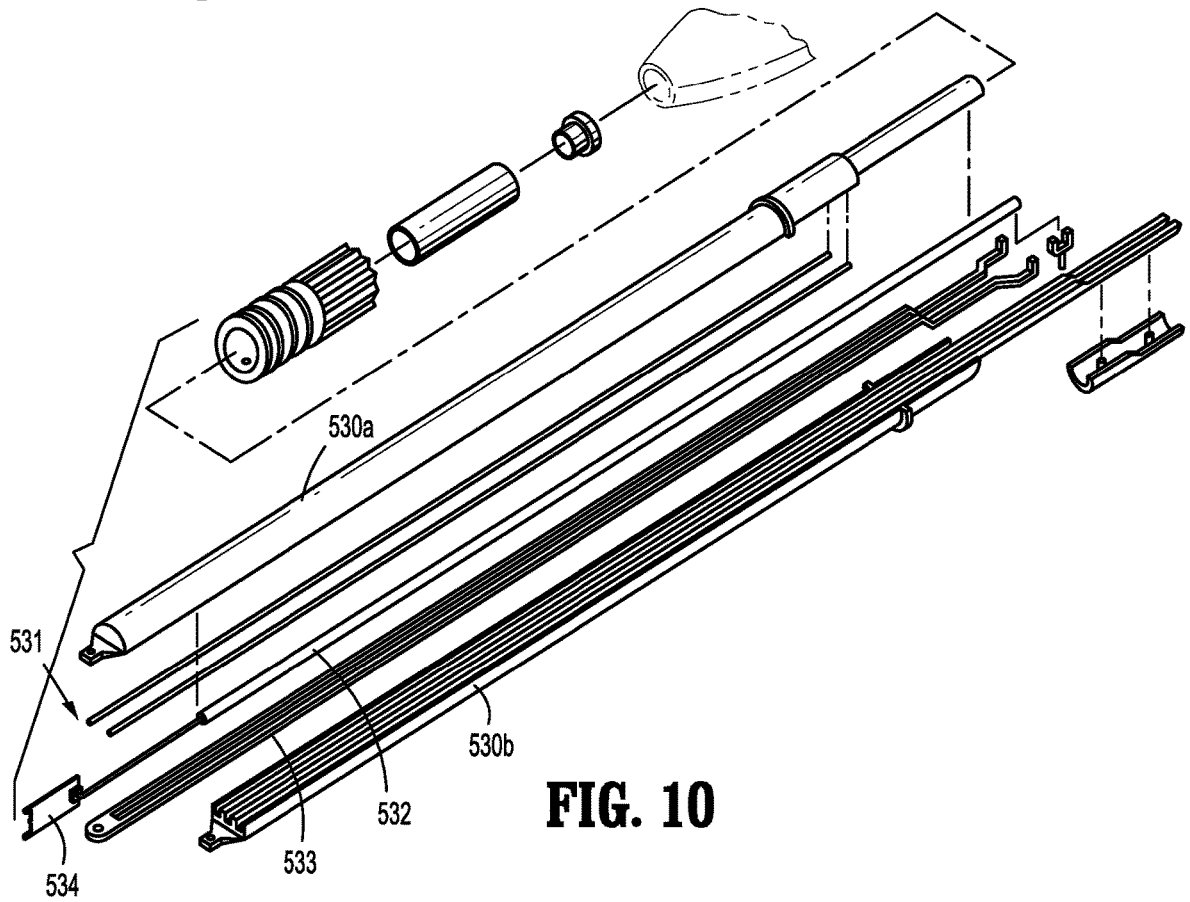
FIG. 10 is an exploded view, with parts separated, of an endoscopic shaft assembly of the fastener applicator of FIG.

Referring to FIG. 10, the endoscopic shaft assembly 530 is shown in an exploded view with parts separated for convenience of illustration and includes an upper housing half section 530*a* and a lower housing half section 530*b*. Positioned within the upper and lower housing half sections 530*a*, 530*b*, is a drive assembly 531. Drive assembly 531 generally includes a pusher or drive beam 532 and an anvil extension 533, and is operatively coupled to the cartridge assembly 540 to engage implantable fasteners 100 supported in the cartridge assembly 540.

Figure 11:
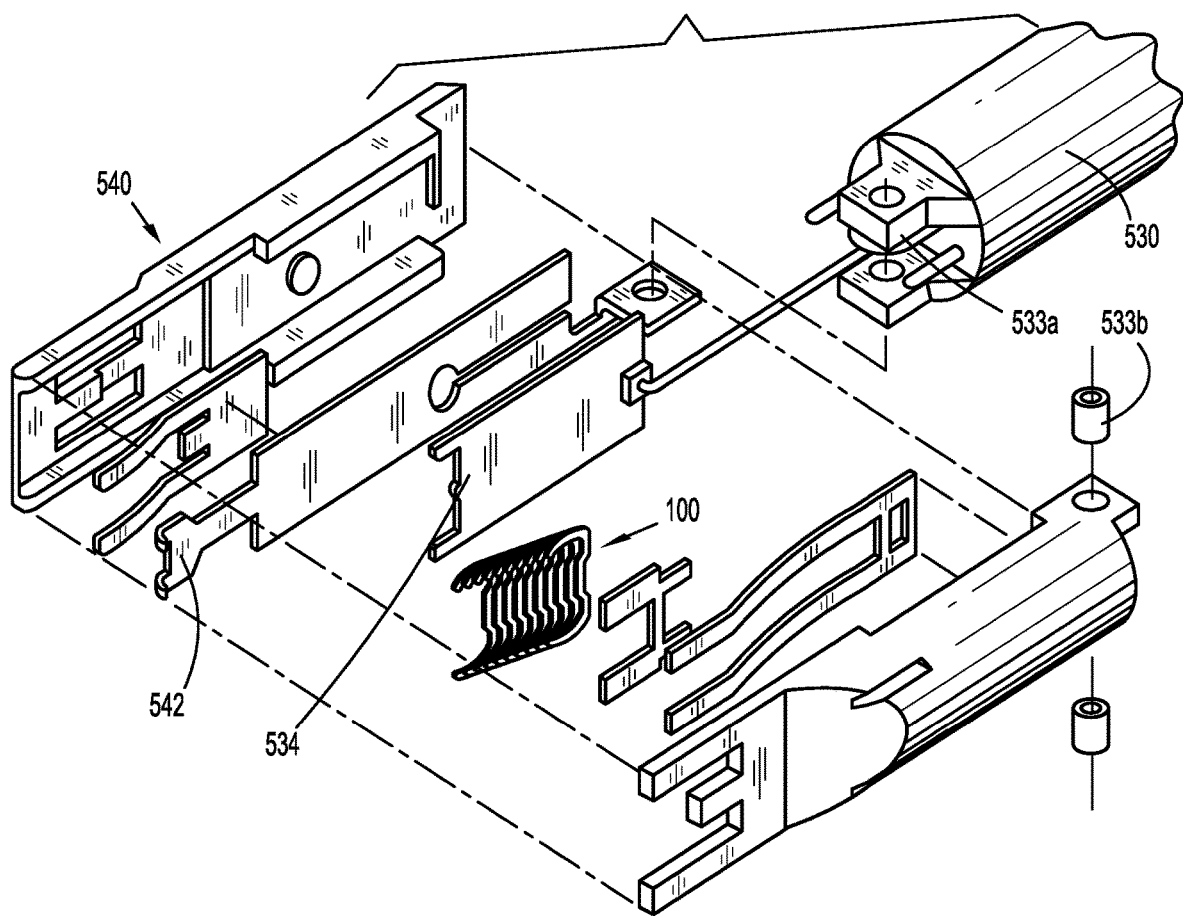
FIG. 11 is an exploded view, with parts separated, of a cartridge assembly of the fastener applicator of FIG.

With additional reference to FIG. 11, drive beam 532 has a pusher plate 534 configured to engage a distal-most implantable fastener 100 of the implantable fasteners 100 upon actuation of the actuation assembly 550. As shown in FIG. 11, anvil extension 533 includes a distal end portion 533*a* that is provided to pivotably couple the cartridge assembly 540 via a pivot pin 533*b*.

With continued reference to FIG. 11, cartridge assembly 540 is adapted to support the implantable fasteners 100. In accordance with the present disclosure, the implantable fasteners 100 are positioned in adjacent stacked relation. In one embodiment, the implantable fasteners 100 are stacked such that an angle of approximately 45 degrees is formed relative to the longitudinal axis "X1-X1" (see FIG. 12). Cartridge assembly 540 further includes an anvil plate 542, for forming the implantable fastener 100 therearound.

Figure 12:
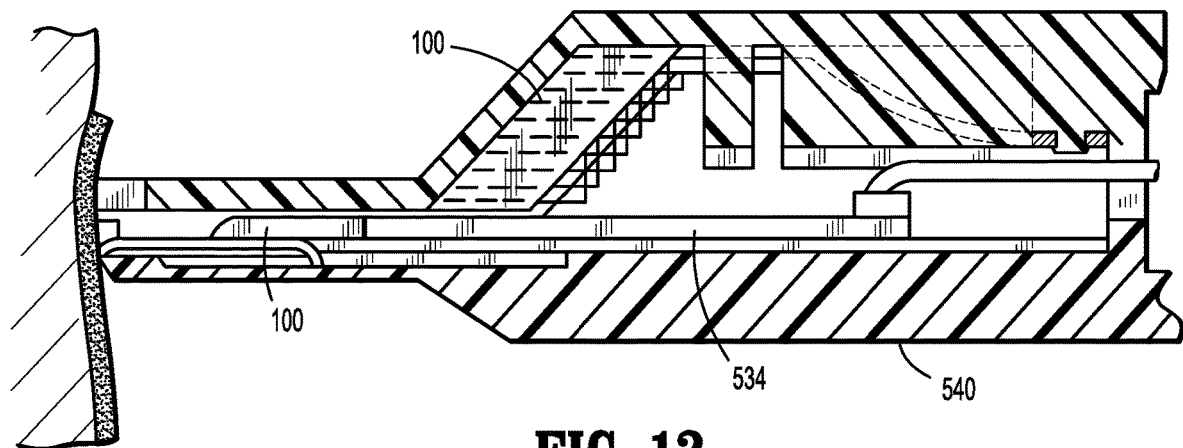
FIG. 12 is a side cross-sectional view of a distal end portion of the cartridge assembly of FIG. 11 prior to firing the implantable fastener.
Figure 13:
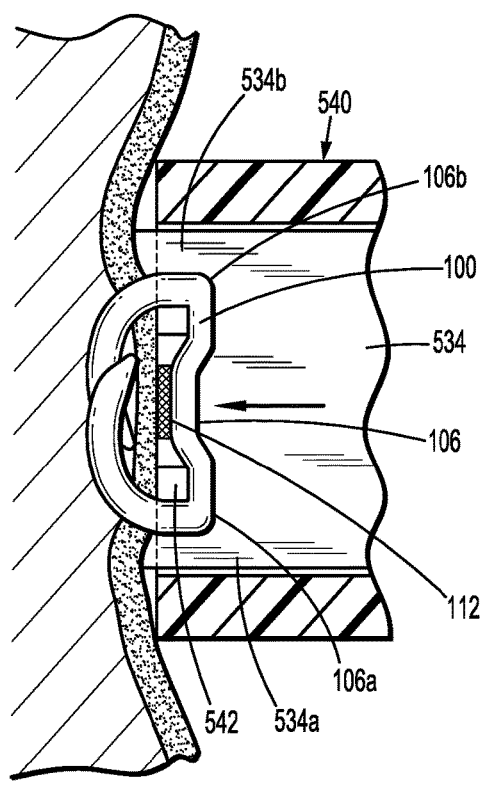
FIG. 13 is a top cross-sectional view of the distal end portion of the cartridge assembly of FIG. 11 illustrating the implantable fastener formed in tissue.

Referring now to FIGS. 12 and 13, advancing and firing of an implantable fastener 100 is illustrated. Upon initial actuation of the actuation assembly 550, the pusher plate 534 is advanced distally and the distal-most implantable fastener 100 is advanced distally of the implantable fasteners 100 in a manner such that pusher plate 534 replaces the distal-most implantable fastener 100 thereby preserving the integrity and position of the stack of the implantable fasteners 100. It is contemplated that pusher plate 534 engages only one implantable fastener 100 at a time.

Upon further actuation of the actuation assembly 550, plusher plate 534 is advanced distally sufficient to cause the distal-most implantable fastener 100 to penetrate tissue and form thereon to secure capsule 112. Specifically, pusher plate 534 includes a pair of lands 534a, 534b to facilitate transmission of advancing force to the first and second end portions 106a, 106b of the backspan 106. Anvil plate 542 is positioned for engagement with backspan 106 such that engagement of implantable fastener 100 by the pair of lands 534a, 534b of pusher plate 534 with the first and second end portions 106a, 106b of the implantable fastener 100 will cause the implantable fastener 100 to form and secure about tissue in a predetermined manner.

Figure 14:
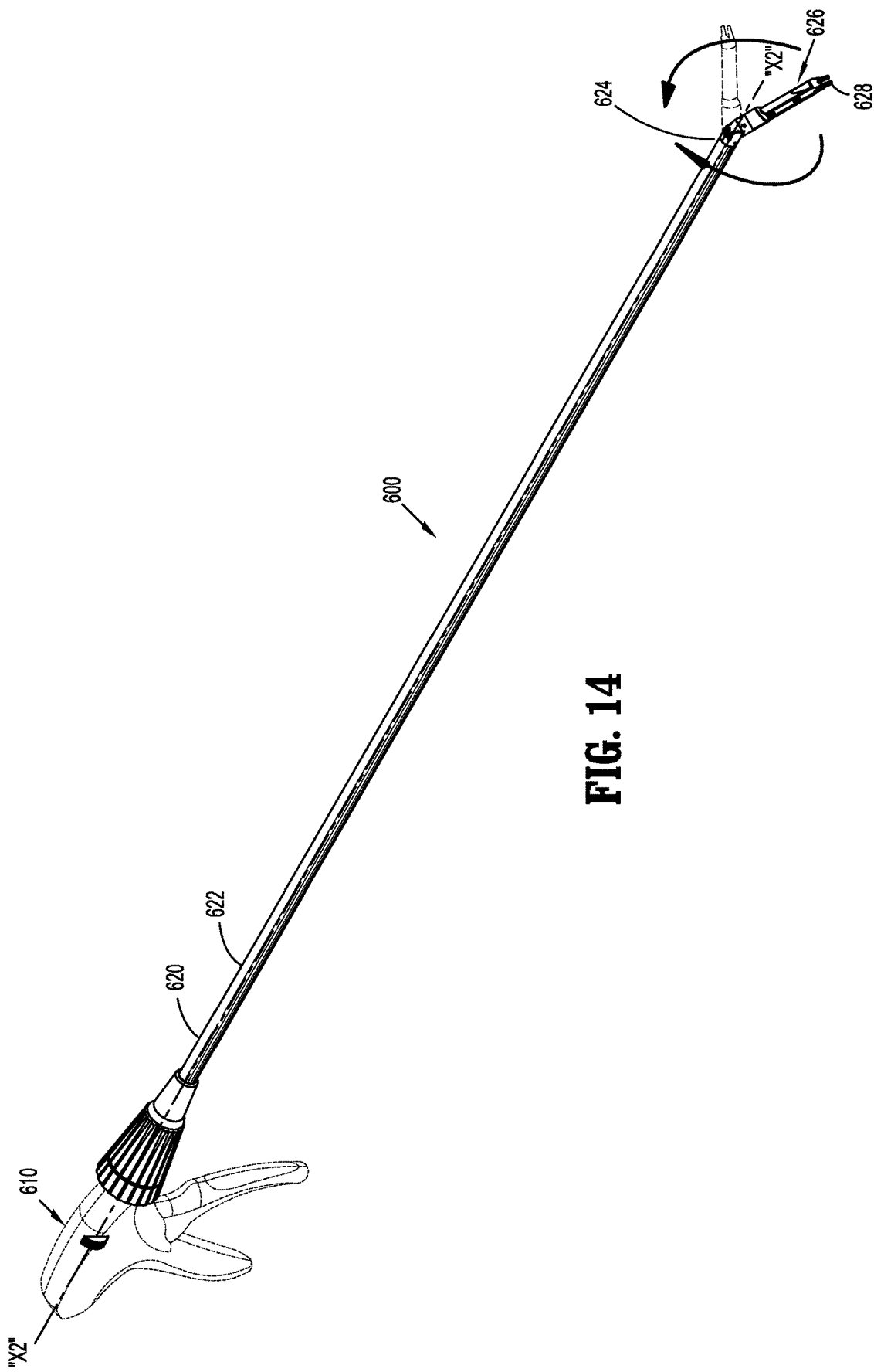
FIG. 14 is a perspective view of a fastener applicator in accordance with another embodiment of the present disclosure, for applying the implantable fasteners of FIGS. 3A-4B.

In order to place implantable fasteners 200, 300 disclosed herein, in accordance with the present disclosure, as illustrated in FIG. 14, a surgical apparatus in the form of a fastener applicator 600 is provided. For a more detailed description of the construction and operation of an example of fastener applicator 600, reference may be made to U.S. Pat. No. 8,403,946, the entire content of which is incorporated herein by reference.

Fastener applicator 600 includes a handle assembly 610, and an endoscopic shaft assembly 620 extending from handle assembly 610. Endoscopic shaft assembly 620 is rotatably connected to handle assembly 610 such that endoscopic shaft assembly 620 is rotatable about a longitudinal axis "X2-X2" thereof. Endoscopic shaft assembly 620 may include a proximal portion 622, and a distal portion 624. An end effector 626 is pivotally connected to distal portion 624, wherein end effector 626 may be articulated relative to distal portion 624.

End effector 626 of endoscopic shaft assembly 620 may include a quantity of implantable fasteners 200, 300 (not shown) pre-loaded therein, or may be configured to selectively receive a cartridge assembly (not shown) which is loaded with a quantity of implantable fasteners 200, 300 therein. For example, the cartridge assembly may be loaded with ten or fewer implantable fasteners 200, 300, or any quantity of implantable fasteners 200, 300.

End effector 626 of endoscopic shaft assembly 620 may include a drive assembly configured to load a single, distal-most implantable fastener 200, 300 into a pair of jaws 628, and to form the implantable fastener 200, 300 loaded into the pair of jaws 628. Fastener applicator 600 is configured to fire and form a single implantable fastener 200, 300 during a complete firing sequence. In any of the embodiments disclosed herein, the fastener instrument can be an open stapler, an endoscopic stapler, clip applier instrument, or other types of surgical instruments. In certain embodiments, the fasteners disclosed herein can be used in a robotic surgical system or with motorized surgical instruments to apply one fastener at a time, or multiple fasteners at a time. In any of the embodiments disclosed herein, the fastener applier can be configured to allow the surgeon to decide how many fasteners to apply, and where, and how many radioactive capsules to apply, or other types of medically or pharmaceutically active capsules to apply.

Figure 15:
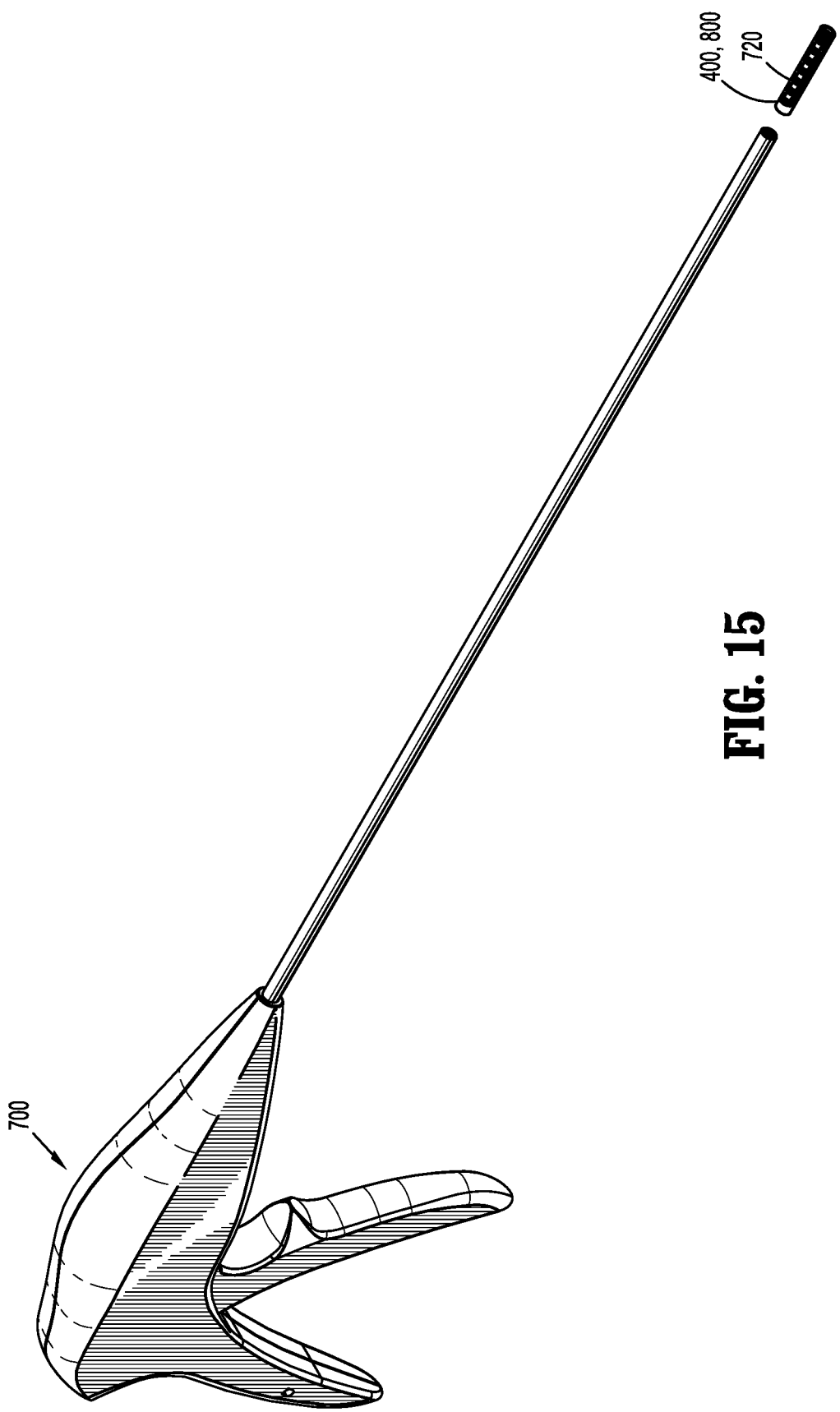
FIG. 15 is a perspective view of a fastener applicator in accordance with another embodiment of the present disclosure, for applying the implantable fasteners of FIGS. 5-8, including an embodiment of a cartridge assembly for loading the implantable fasteners of FIGS. 5-8.

In order to place implantable fasteners 400, 800, 900 in accordance with the present disclosure, as illustrated in FIG. 15, a surgical apparatus in the form of a fastener applicator 700 is provided. For a more detailed description of the construction and operation of an example of a fastener applicator 700 capable of firing implantable fasteners 400, 800, 900 reference may be made to U.S. Pat. No. 5,830,221, the entire content of which is incorporated herein by reference. Fastener applicator 700 may be provided either preloaded with implantable fasteners 400, 800, or may be configured to selectively receive a cartridge assembly 720 loaded with implantable fasteners 400, 800.

With reference to FIG. 16, in embodiments, the fastener applicator 700 (FIG. 15) may be configured to selectively receive cartridge assembly 720' preloaded with a plurality of implantable fasteners 900. Cartridge assembly 720' includes a plurality of ports 740 extending through an outer surface thereof. Each port 740 is configured and dimensioned to longitudinally align with the respective cannula 902c of body 902 of each implantable fastener 900 preloaded into the cartridge assembly 720'. With the plurality of implantable fasteners 900 preloaded into the cartridge assembly 720', the plurality of capsules 912 may be inserted through the plurality of ports 740 and disposed within the respective cannulas 902c of the plurality of implantable fasteners 900. This configuration facilitates efficient loading of the plurality of implantable fasteners 900 with the plurality of capsules 912 without having to handle each implantable fastener 900 individually. It is contemplated that this configuration may facilitate field customization of the payload.

The fastener applicator 700 may be configured to fire or deliver implantable fasteners 400, 800, 900 during a full firing sequence. The fastener applicator 700 may also be configured to articulate in order to facilitate the firing of implantable fasteners 400, 800, 900 therefrom.

In accordance with the present disclosure, the combination of implantable fasteners and fastener applicators disclosed herein provides a clinician a relatively great deal of flexibility and customization in placing radiation emitting implants, such as, for example, implantable fasteners 100, 200, 300, 400, 800, 900 at desired target surgical sites, whereby the fastener applicator, such as, for example, fastener applicator 500 is articulatable and/or rotatable to provide the clinician with increased flexibility and precision in placing the radiation emitting implants. It is also contemplated that the fasteners could dispense other types of medical treatments such as pharmaceutically active agents.

It is contemplated for example, that a geometry of implantable fasteners 100, 200, 300, 400, 800, 900; and a geometry of a fastener applicator 500, 600, 700 may be optimized to work together as location guides to optimally place implantable fasteners 100, 200, 300, 400, 800, 900 adjacent to one another, wherein the capsules 112, 212, 316, 410, 410', 810, 912 has a known geometry and radiation field strength, to achieve effective dosimetry.

In accordance with the present disclosure, the location of placement of implantable fasteners 100, 200, 300, 400, 800, 900 is not limited to a predefined geometry, pattern, density, or the like. In particular, as mentioned above, implantable fasteners 100, 200, 300, 400, 800, 900 may be fastened to a target tissue site in any geometry, pattern and/or density, as the clinician desires or needs.

By way of example, the ability to fasten implantable fasteners 100, 200, 300, 400, 800, 900 to a target tissue site, such as, for example, lung tissue in a lung resection procedure, in any geometry, pattern and/or density, may be quite useful in a lung cancer patient, where many lung cancer patients suffer from impaired lung volume and cannot tolerate unnecessary loss of lung volume, and may need multiple rows of brachytherapy sources to ensure treatment of an inadequately narrow surgical margin.

In any of the embodiments disclosed herein, the implantable fasteners 100, 200, 300, 400, 800, 900 may be incorporated into, or configured for use with, devices that are part of a powered surgical system or robotic surgical system.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended thereto.

What is claimed is:

1. A fastener applicator comprising: a body portion including a handle assembly;
   a cartridge assembly supported within the body portion, the cartridge assembly including implantable fasteners, at least one implantable fastener having:
   a body including a backspan having a tissue facing surface;
   a tissue penetrating portion extending from the body, the tissue penetrating portion including:
   a first leg having first and second portions and a first connecting portion interconnecting the first and second portions, the first portion extending from a first end portion of the backspan and coupled to the second portion extending towards the backspan; and
   a second leg having third and fourth portions and a second connecting portion interconnecting the third and fourth portions, the third portion extending from a second end portion of the backspan and coupled to the fourth portion, the first and third portions of the respective first and second legs extending away from the backspan at an angle such that the first and third portions of the respective first and second legs overlap one another, the backspan being spaced apart from the first and second connecting portions of the respective first and second legs in an unformed condition, and the backspan and the first and third portions of the respective first and second legs being parallel to each other in a formed condition; and
   a capsule affixed to the tissue facing surface of the body, the capsule including radioactive material;
   a drive assembly supported within the body portion and operatively coupled to the cartridge assembly to engage the implantable fasteners; and
   an actuation assembly supported within the handle assembly and operatively coupled to the drive assembly to fire a distal-most implantable fastener upon actuation of the actuation assembly.

2. The fastener applicator according to claim 1, wherein at least one of the implantable fasteners is a surgical staple and includes a radioactive material configured to provide a dose of radiation to a target surgical site.

3. The fastener applicator according to claim 2, wherein the tissue facing surface defines a flattened surface extending along at least a portion thereof, the flattened surface providing an increased surface area for affixing the capsule onto the tissue facing surface of the backspan.

4. The fastener applicator according to claim 1, wherein a radioactive material is dispersed throughout at least one of the implantable fasteners such that the entirety of the at least one of the implantable fasteners emits radiation.

5. The fastener applicator according to claim 1, wherein the implantable fasteners include a first implantable fastener having sufficient mechanical strength to hold tissue together, and a second implantable fastener having the capsule affixed thereon for providing a dose of radiation to a target surgical site.

6. The fastener applicator according to claim 1 wherein at least a portion of the second portion of the first leg and at least a portion of the fourth portion of the second leg are radiused and in relative close approximation to one another in the formed condition of the at least one implantable fastener.

7. The fastener applicator according to claim 1, wherein in the unformed condition, the backspan is distal of the first and second connecting portions of the first and second legs respectively.

8. A method of performing a surgical procedure at a surgical site, the method comprising:
   positioning a fastener applicator within an opening in tissue, the fastener applicator loaded with implantable fasteners, each implantable fastener including:
   a body including a backspan having a tissue facing surface;
   a tissue penetrating portion extending from the body, the tissue penetrating portion including:
   a first leg having first and second portions and a first connecting portion interconnecting the first and second portions, the first portion extending from a first end portion of the backspan and coupled to the second portion extending towards the backspan; and
   a second leg having third and fourth portions and a second connecting portion interconnecting the third and fourth portions, the third portion extending from a second end portion of the backspan and coupled to the fourth portion, the first and third portions of the respective first and second legs extending away from the backspan at an angle such that the first and third portions of the respective first and second legs overlap one another, the backspan being spaced apart from the first and second connecting portions of the respective first and second legs in an unformed condition, and the backspan and the first and third portions of the respective first and second legs being parallel to each other in a formed condition; and
   a capsule affixed to the tissue facing surface of the body, the capsule including radioactive material;
   locating a first target of the surgical site; and
   firing the fastener applicator to secure a first implantable fastener to the first target of the surgical site such that the capsule affixed thereon is in contact with tissue adjacent the first target of the surgical site.

9. The method according to claim 8, further comprising:
   locating a second target of the surgical site;
   relocating the fastener applicator to the second target of the surgical site; and
   firing the fastener applicator to secure a second implantable fastener to the second target such that the capsule affixed thereon is in contact with tissue adjacent the second target of the surgical site.

10. The method according to claim 9, further comprising:
    locating a plurality of targets of the surgical site;
    relocating the fastener applicator to the plurality of targets of the surgical site; and
    securing the implantable fasteners in any configuration, in any pattern, or in any quantity.

* * * * *